US007160709B2

(12) United States Patent
Wang

(10) Patent No.: US 7,160,709 B2
(45) Date of Patent: Jan. 9, 2007

(54) PHENOL OXIDIZING ENZYMES

(75) Inventor: Huaming Wang, Fremont, CA (US)

(73) Assignee: Genencor International, Inc., Palo Alto, CA (US)

( * ) Notice: Subject to any disclaimer, the term of this patent is extended or adjusted under 35 U.S.C. 154(b) by 177 days.

(21) Appl. No.: 10/997,247

(22) Filed: Nov. 24, 2004

(65) Prior Publication Data

US 2005/0244923 A1 Nov. 3, 2005

Related U.S. Application Data

(63) Continuation of application No. 10/080,233, filed on Feb. 19, 2002, now abandoned, which is a continuation of application No. 09/218,702, filed on Dec. 22, 1998, now Pat. No. 6,426,410.

(51) Int. Cl.
*C12N 9/02* (2006.01)
*C12N 15/53* (2006.01)
*C12N 15/79* (2006.01)

(52) U.S. Cl. .................. 435/189; 435/69.1; 435/252.3; 435/320.1

(58) Field of Classification Search ..................... None
See application file for complete search history.

(56) References Cited

U.S. PATENT DOCUMENTS

| | | | | |
|---|---|---|---|---|
| 6,168,936 | B1 * | 1/2001 | Wang | 435/189 |
| 6,399,329 | B1 * | 6/2002 | Wang et al. | 435/69.1 |
| 6,509,307 | B1 * | 1/2003 | Bodie et al. | 510/226 |
| 6,905,853 | B1 * | 6/2005 | Wang | 435/189 |

FOREIGN PATENT DOCUMENTS

| | | | |
|---|---|---|---|
| JP | 5-199882 | * | 8/1993 |
| WO | WO 99/49010 | * | 9/1999 |
| WO | WO 99/49020 | * | 9/1999 |

OTHER PUBLICATIONS

Koikeda, S. et al., 1993, "Molecular cloning of the gene for bilirubin oxidase from *Myrothecium verrucafia* and its expression in yeast," Journal of Biological Chemistry, vol. 268, No. 25, pp. 18801-18809.*

* cited by examiner

*Primary Examiner*—Nashaat T. Nashed
*Assistant Examiner*—William W. Moore
(74) *Attorney, Agent, or Firm*—Lynn Marcus-Wyner

(57) ABSTRACT

Disclosed herein are novel phenol oxidizing enzymes naturally-produced by strains of the species *Stachybotrys* which possess a pH optima in the alkaline range and which are useful in modifying the color associated with dyes and colored compounds, as well as in anti-dye transfer applications. Also disclosed herein are biologically-pure cultures of strains of the genus *Stachybotrys*, designated herein *Stachybotrys parvispora* MUCL 38996 and *Stachybotrys chartarum* MUCL 38898, which are capable of naturally-producing the novel phenol oxidizing enzymes.

Disclosed herein is the amino acid and nucleic acid sequence for *Stachybotrys* phenol oxidizing enzymes as well as expression vectors and host cells comprising the nucleic acid. Disclosed herein are methods for producing the phenol oxidizing enzyme as well as methods for constructing expression hosts.

4 Claims, 6 Drawing Sheets

GTCAATATGCTGTTCAAGTCATGGCAACTGGCAGCAGCCTCCGGGCTCCTGTCTGGAGTCCTCGGCATCCCGATGGACACCGGCAGCCAC 90
M L F K S W Q L A A A S G L L S G V L G I P M D T G S H 28

CCCATTGAGGCTGTTGATCCCGAAGTGAAGACTGAGGTCTTCGCTGACTCCCTCCTTGCTGCAGCAGGCGATGACGACTGGGAGTCACCT 180
P I E A V D P E V K T E V F A D S L L A A A G D D D W E S P 58

CCATACAACTTGCTTTACAGGAATGCCCTGCCAATTCCACCTGTCAAGCAGCCCAAGATGATCATTACCAACCCTGTCACCGGCAAGGAC 270
P Y N L L Y R N A L P I P P V K Q P K M I I T N P V T G K D 88

ATTTGGTACTATGAGATCGAGATCAAGCCATTTCAGCAAAGGATTTACCCCACCTTGCGCCCTGCCACTCTCGTCGGCTACGATGGCATG 360
I W Y Y E I E I K P F Q Q R I Y P T L R P A T L V G Y D G M 118

AGCCCTGGTCCTACTTTCAATGTTCCCAGAGGAACAGAGACTGTAGTTAGGTTCATCAACAATGCCACCGTGGAGAACTCGGTCCATCTG 450
S P G P T F N V P R G T E T V V R F I N N A T V E N S V H L 148

CACGGCTCCCCATCGCGTGCCCCTTTCGATGGTTGGGCTGAAGATGTGACCTTCCCTGGCGAGTACAAGGATTACTACTTTCCCAACTAC 540
H G S P S R A P F D G W A E D V T F P G E Y K D Y Y F P N Y 178

CAATCCGCCCGCCTTCTGTGGTACCATGACCACGCTTTCATGAAGACTGCTGAGAATGCCTACTTTGGTCAGGCTGGCGCCTACATTATC 630
Q S A R L L W Y H D H A F M K T A E N A Y F G Q A G A Y I I 208

AACGACGAGGCTGAGGATGCTCTCGGTCTTCCTAGTGGCTATGGCGAGTTCGATATCCCTCTGATCCTGACGGCCAAGTACTATAACGCC 720
N D E A E D A L G L P S G Y G E F D I P L I L T A K Y Y N A 238

GATGGTACCCTGCGTTCGACCGAGGGTGAGGACCAGGACCTGTGGGGAGATGTCATCCATGTCAACGGACAGCCATGGCCTTTCCTTAAC 810
D G T L R S T E G E D Q D L W G D V I H V N G Q P W P F L-N 268

GTCCAGCCCCGCAAGTACCGTTTCCGATTCCTCAACGCTGCCGTGTCTCGTGCTTGGCTCCTCTACCTCGTCAGGACCAGCTCTCCCAAC 900
V Q P R K Y R F R F L N A A V S R A W L L Y L V R T S S P N 298

GTCAGAATTCCTTTCCAAGTCATTGCCTCTGATGCTGGTCTCCTTCAAGCCCCCGTTCAGACCTCTAACCTCTACCTTGCTGTTGCCGAG 990
V R I P F Q V I A S D A G L L Q A P V Q T S N L Y L A V A E 328

CGTTACGAGATCATTATTGACTTCACCAACTTTGCTGGCCAGACTCTTGACCTGCGCAACGTTGCTGAGACCAACGATGTCGGCGACGAG 1080
R Y E I I I D F T N F A G Q T L D L R N V A E T N D V G D E 358

GATGAGTACGCTCGCACTCTCGAGGTGATGCGCTTCGTCGTCAGCTCTGGCACTGTTGAGGACAACAGCCAGGTCCCCTCCACTCTCCGT 1170
D E Y A R T L E V M R F V V S S G T V E D N S Q V P S T L R 388

GACGTTCCTTTCCCTCCTCACAAGGAAGGCCCCGCCGACAAGCACTTCAAGTTTGAACGCAGCAACGGACACTACCTGATCAACGATGTT 1260
D V P F P P H K E G P A D K H F K F E R S N G H Y L I N D V 418

GGCTTTGCCGATGTCAATGAGCGTGTCCTGGCCAAGCCCGAGCTCGGCACCGTTGAGGTCTGGGAGCTCGAGAACTCCTCTGGAGGCTGG 1350
G F A D V N E R V L A K P E L G T V E V W E L E N S S G G W 448

AGCCACCCCGTCCACATTCACCTTGTTGACTTCAAGATCCTCAAGCGAACTGGTGGTCGTGGCCAGGTCATGCCCTACGAGTCTGCTGGT 1440
S H P V H I H L V D F K I L K R T G G R G Q V M P Y E S A G 478

CTTAAGGATGTCGTCTGGTTGGGCAGGGGTGAGACCCTGACCATCGAGGCCCACTACCAACCCTGGACTGGAGCTTACATGTGGCACTGT 1530
L K D V V W L G R G E T L T I E A H Y Q P W T G A Y M W H C 508

CACAACCTCATTCACGAGGATAACGACATGATGGCTGTATTCAACGTCACCGCCATGGAGGAGAAGGGATATCTTCAGGAGGACTTCGAG 1620
H N L I H E D N D M M A V F N V T A M E E K G Y L Q E D F E 538

GACCCCATGAACCCCAAGTGGCGCGCCGTTCCTTACAACCGCAACGACTTCCATGCTCGCGCTGGAAACTTCTCCGCCGAGTCCATCACT 1710
D P M N P K W R A V P Y N R N D F H A R A G N F S A E S I T 568

GCCCGAGTGCAGGAGCTGGCCGAGCAGGAGCCGTACAACCGCCTCGATGAGATCCTGGAGGATCTTGGAATCGAGGAGTAA 1791
A R V Q E L A E Q E P Y N R L D E I L E D L G I E E 594

Figure 1

CTGGCTAGCC TCACTTGGTA GACAGCCCTG ACAGCCTCAC TGGCTGGGGG TCGAAAGGCC AGTCAATATC TTGGTCACTG 80
CTAATAGTTC CTTGCTACGC GCAAAAAGCT CCTTGCCGAA GGGGCACAGA CTATCAAGTG AGACATATAG GATGCATGTC 160
TTTCATAGCC ACAGTTAGGG TGGTGACCTA CTCGAAGAGG CCCCGACTTG CATGCATACG ACATGTCGCT TCCATGCAAC 240
ATGTATGCGC ACATCGGCGA TCAGGCACCC TCTGCATGCA GAATAGAACC CCCCTGGTTT CCTTTTGTTT CTTTTCCTTT 320
CTCAACGACG CGTGAGCGTG GTTAACTTGA GCAAGGCCGA GTGGTCTGTT CACGAGGTTA CCATCGAACT CTCTTCTTTC 400
CCAATCATGA CCTGCCCCCC GAGTTTAGCC CCCATCACGG CTGTGAAATC CACTTCGATA ATCCTAGCCT AGTGCTACTC 480
TTCAATAGTT GCTCCTGATG GGGCACTTTG GTCACATTGC CTTGGTTYCT CCTACCTCGT TCTCTTCCGC ATCAAGCCTC 560
TATGCCCGAC GACAACACCT CATTGGCCCG GACCACTTTG AGCGCGCACG CACCTTCGCG CCGAAGGAGT TGATAACACC 640
CTTCACCCTT GCCCAATGAT GGAGTTTTGG TCTATTTGTC ATGATCACCT CACATTCACT AGATCACGGA TCCTGGAAGA 720
GGGTGTGGAA GCCAGACCAG CTTGTCCCTG TTCTTGCAGA CTCAGGTCAG CTCCTAGCGG CTATCACAGC TCAGGATTAT 800
CAAGTCCCGT AAAGTCCAGA CCCTTTTCAT TGTATGATGC TGCCTAATTT GCGCTATCTC TATGCCGTAG CAGCCGTCTT 880
GGCTACAACT GGCTGCCATG GCTGAAGCAT CGTGAGATCT ATAAAGGTCT CCGAATCCTC GGTGAAGTCA GAATCGTCTC 960
TCCACACCAG TCAACAACAA GCTTCTTTCT CTTACAGCTT AGCCTGAGCA CATTCACAGA ACTCTTCCCT TCTTTTCGTC 1040
AATATGCTGT TCAAGTCATG GCAACTGGCA GCAGCCTCCG GGCTCCTGTC TGGAGTCCTC GGCATCCCGA TGGACACCGG 1120
CAGCCACCCC ATTGAGGCTG TTGATCCCGA AGTGAAGACT GAGGTCTTCG CTGACTCCCT CCTTGCTGCA GCAGGCGATG 1200
ACGACTGGGA GTCACCTCCA TACAACTTGC TTTACAGGTG AGACACCTGT CCCACCTGTT TTCCCTCGAT AACTAACTCT 1280
TATAGGAATG CCCTGCCAAT TCCACCTGTC AAGCAGCCCA AGATGTATGT CTTTGATTTT CTACGAAGCA ACTCGGCCCC 1360
GACTAATGTA TTCTAGGATC ATTACCAACC CTGTCACCGG CAAGGACATT TGGTACTATG AGATCGAGAT CAAGCCATTT 1440
CAGCAAAGGG TGAGTTTGCT CAGAAACCTT GTGGTAATTA ATCATTGTTA CTGACCCTTT CAGATTTACC CCACCTTGCG 1520
CCCTGCCACT CTCGTCGGCT ACGATGGCAT GAGCCCTGGT CCTACTTTCA ATGTTCCCAG AGGAACAGAG ACTGTAGTTA 1600
GGTTCATCAA CAATGCCACC GTGGAGAACT CGGTCCATCT GCACGGCTCC CCATCGCGTG CCCCTTTCGA TGGTTGGGCT 1680
GAAGATGTGA CCTTCCCTGG CGAGTACAAG GATTACTACT TTCCCAACTA CCAATCCGCC CGCCTTCTGT GGTACCATGA 1760
CCACGCTTTC ATGAAGGTAT GCTACGAGCC TTTATCTTTC TTGGCTACCT TTGGCTAACC AACTTCCTTT CGTAGACTGC 1840
TGAGAATGCC TACTTTGGTC AGGCTGGCGC CTACATTATC AACGACGAGG CTGAGGATGC TCTCGGTCTT CCTAGTGGCT 1920
ATGGCGAGTT CGATATCCCT CTGATCCTGA CGGCCAAGTA CTATAACGCC GATGGTACCC TGCGTTCGAC CGAGGGTGAG 2000
GACCAGGACC TGTGGGGAGA TGTCATCCAT GTCAACGGAC AGCCATGGCC TTTCCTTAAC GTCCAGCCCC GCAAGTACCG 2080
TTTCCGATTC CTCAACGCTG CCGTGTCTCG TGCTTGGCTC CTCTACCTCG TCAGGACCAG CTCTCCCAAC GTCAGAATTC 2160
CTTTCCAAGT CATTGCCTCT GATGCTGGTC TCCTTCAAGC CCCCGTTCAG ACCTCTAACC TCTACCTTGC TGTTGCCGAG 2240
CGTTACGAGA TCATTATTGG TATGCCCTCC CCTCTCACGA ATGAGTCAAG AACTCTAAGA CTAACACTTG TAGACTTCAC 2320
CAACTTTGCT GGCCAGACTC TTGACCTGCG CAACGTTGCT GAGACCAACG ATGTCGGCGA CGAGGATGAG TACGCTCGCA 2400
CTCTCGAGGT GATGCGCTTC GTCGTCAGCT CTGGCACTGT TGAGGACAAC AGCCAGGTCC CCTCCACTCT CCGTGACGTT 2480
CCTTTCCCTC CTCACAAGGA AGGCCCCGCC GACAAGCACT TCAAGTTTGA ACGCAGCAAC GGACACTACC TGATCAACGA 2560
TGTTGGCTTT GCCGATGTCA ATGAGCGTGT CCTGGCCAAG CCCGAGCTCG GCACCGTTGA GGTCTGGGAG CTCGAGAACT 2640
CCTCTGGAGG CTGGAGCCAC CCCGTCCACA TTCACCTTGT TGACTTCAAG ATCCTCAAGC GAACTGGTGG TCGTGGCCAG 2720
GTCATGCCCT ACGAGTCTGC TGGTCTTAAG GATGTCGTCT GGTTGGGCAG GGGTGAGACC CTGACCATCG AGGCCCACTA 2800
CCAACCCTGG ACTGGAGCTT ACATGTGGCA CTGTCACAAC CTCATTCACG AGGATAACGA CATGATGGCT GTATTCAACG 2880
TCACCGCCAT GGAGGAGAAG GGATATCTTC AGGAGGACTT CGAGGACCCC ATGAACCCCA AGTGGCGCGC CGTTCCTTAC 2960
AACCGCAACG ACTTCCATGC TCGCGCTGGA AACTTCTCCG CCGAGTCCAT CACTGCCCGA GTGCAGGAGC TGGCCGAGCA 3040
GGAGCCGTAC AACCGCCTCG ATGAGATCCT GGAGGATCTT GGAATCGAGG AGTAAACCCC GAGCCACAAG CTCTACAATC 3120
GTTTTGAGTC TTAAGACGAG GCTCTTGGTG CGTATTCTTT TCTTCCCTAC GGGGAACTCC GCTGTCCACT GCGATGTGAA 3200
GGACCATCAC AAAGCAACGT ATATATTGGA CTCACCACTG TCATTACCGC CCACTTGTAC CTATTCGATT CTTGTTCAAA 3280
CTTTTCTAGT GCGAGAGTGT CCATAGTCAA GAAACGCCCA TAGGGCTATC GTCTAAACTG AACTATTGTG TGGTCTGTGA 3360
CGTGGAGTAG ATGTCAATTG TGATGAGACA CAGTAAATAC GGTATATCTT TTCCTAGGAC TACAGGATCA GTTTCTCATG 3440
AGATTACATC CGTCTAATGT TTGTCCATGA GAGTCTAGCT AAGGTTGAGA ATGCATCAGA CGGAATCATT TGATGCTCTC 3520
AGCTCGTATT ACCGATGTAA GACAAGTTAG GTAAGTTGCT TGGTATCCGA AAATGACTCA GGCTCCCTCA TTAGGTTGCA 3600
TGTGAAAACC TTCAGCAACT CATGGGTGTT GGGACCAAAT CATCCATACC TGATTTTGAT AACTGACCTG GGTCAAT 3677

Figure 2

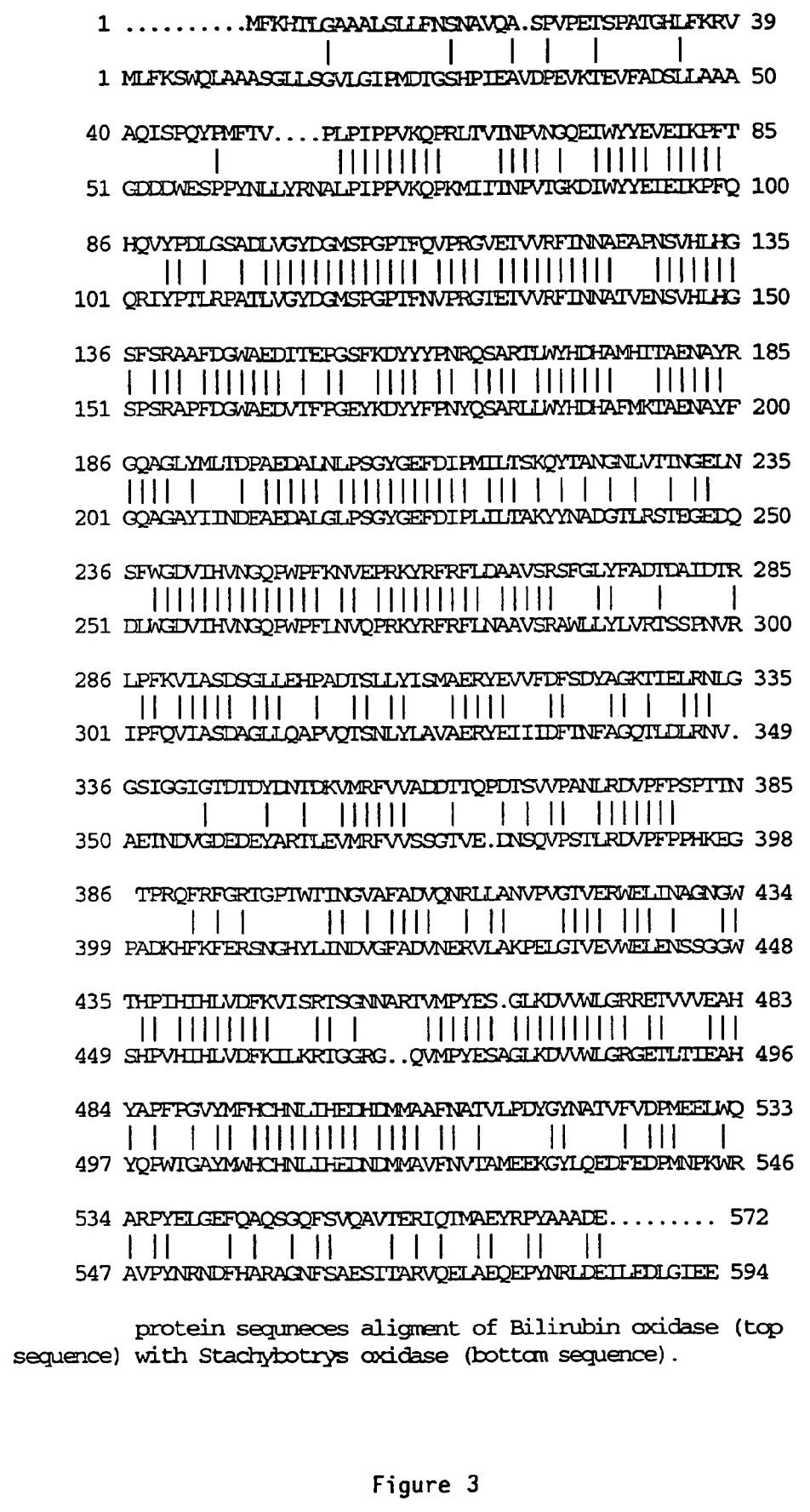

```
  1 ..........MFKHTLGAAALSLLFNSNAVQA.SPVPETSPATGHLFKRV 39
  1 MLFKSWQLAAASGLLSGVLGIPMDTGSHPIEAVDPEVKTEVFADSLLAAA 50

 40 AQISPQYPMFTV....PLPIPPVKQPRLTVINPVNGQEIWYYEVEIKPFT 85
 51 GDDDWESPPYNLLYRNALPIPPVKQPKMITINPVIGKDIWYYEIEIKPFQ 100

 86 HQVYPDLGSADLVGYDGMSPGPTFQVPRGVETVVRFINNAEAPNSVHLHG 135
101 QRIYPTLRPATLVGYDGMSPGPTFNVPRGIETVVRFINNATVENSVHLHG 150

136 SFSRAAFDGWAEDITEPGSFKDYYYPNRQSARTLWYHDHAMHITAENAYR 185
151 SPSRAPFDGWAEDVTFPGEYKDYYFPNYQSARLLWYHDHAFMKTAENAYF 200

186 GQAGLYMLTDPAEDALNLPSGYGEFDIPMILTSKQYTANGNLVTTNGELN 235
201 GQAGAYIINDEAEDALGLPSGYGEFDIPLILTAKYYNADGTLRSTEGEDQ 250

236 SFWGDVIHVNGQPWPFKNVEPRKYRFRFLDAAVSRSFGLYFADTDAIDTR 285
251 DLWGDVIHVNGQPWPFLNVQPRKYRFRFLNAAVSRAWLLYLVRTSSPNVR 300

286 LPFKVIASDSGLLEHPADTSLLYISMAERYEVVFDFSDYAGKTIELRNLG 335
301 IPFQVIASDAGLLQAPVQTSNLYLAVAERYEIIIDFINFAGQTLDLRNV. 349

336 GSIGGIGTDTDYDNTDKVMRFVVADDTTQPDTSVVPANLRDVPFPSPTTN 385
350 AEINDVGDEDEYARTLEVMRFVVSSGTVE.DNSQVPSTLRDVPFPPHKEG 398

386  TPRQFRFGRTGPTWTTNGVAFADVQNRLLANVPVGTVERWELINAGNGW 434
399 PADKHFKFERSNGHYLINDVGFADVNERVLAKPELGIVEVWELENSSGGW 448

435 THPIHIHLVDFKVISRTSGNNARTVMPYES.GLKDVVWLGRRETVVVEAH 483
449 SHPVHIHLVDFKILKRTGGRG..QVMPYESAGLKDVVWLGRGETLTIEAH 496

484 YAPFPGVYMFHCHNLIHEDHDMMAAFNATVLPDYGYNATVFVDPMEELWQ 533
497 YQPWTGAYMWHCHNLIHEDNDMMAVFNVTAMEEKGYLQEDFEDPMNPKWR 546

534 ARPYELGEFQAQSGQFSVQAVTERIQTMAEYRPYAAADE......... 572
547 AVPYNRNDFHARAGNFSAESTTARVQELAEQEPYNRLDEILEDLGIEE 594
```

protein sequneces aligment of Bilirubin oxidase (top sequence) with Stachybotrys oxidase (bottom sequence).

Figure 3

```
AGATCTAATA TGCTGTTCAA GTCATGGCAA CTGGCAGCAG CCTCCGGGCT CCTGTCTGGA 60
GTCCTCGGCA TCCCGATGGA CACCGGCAGC CACCCCATTG AGGCTGTTGA TCCCGAAGTG 120
AAGACTGAGG TCTTCGCTGA CTCCCTCCTT GCTGCAGCAG GCGATGACGA CTGGGAGTCA 180
CCTCCATACA ACTTGCTTTA CAGGTGAGAC ACCTGTCCCA CCTGTTTTCC CTCGATAACT 240
AACTCTTATA GGAATGCCCT GCCAATTCCA CCTGTCAAGC AGCCCAAGAT GTATGTCTTT 300
GATTTTCTAC GAAGCAACTC GGCCCCGACT AATGTATTCT AGGATCATTA CCAACCCTGT 360
CACCGGCAAG GACATTTGGT ACTATGAGAT CGAGATCAAG CCATTTCAGC AAAGGGTGAG 420
TTTGCTCAGA AACCTTGTGG TAATTAATCA TTGTTACTGA CCCTTTCAGA TTTACCCCAC 480
CTTGCGCCCT GCCACTCTCG TCGGCTACGA TGGCATGAGC CCTGGTCCTA CTTTCAATGT 540
TCCCAGAGGA ACAGAGACTG TAGTTAGGTT CATCAACAAT GCCACCGTGG AGAACTCGGT 600
CCATCTGCAC GGCTCCCCAT CGCGTGCCCC TTTCGATGGT TGGGCTGAAG ATGTGACCTT 660
CCCTGGCGAG TACAAGGATT ACTACTTTCC CAACTACCAA TCCGCCCGCC TTCTGTGGTA 720
CCATGACCAC GCTTTCATGA AGGTATGCTA CGAGCCTTTA TCTTTCTTGG CTACCTTTGG 780
CTAACCAACT TCCTTTCGTA GACTGCTGAG AATGCCTACT TTGGTCAGGC TGGCGCCTAC 840
ATTATCAACG ACGAGGCTGA GGATGCTCTC GGTCTTCCTA GTGGCTATGG CGAGTTCGAT 900
ATCCCTCTGA TCCTGACGGC CAAGTACTAT AACGCCGATG GTACCCTGCG TTCGACCGAG 960
GGTGAGGACC AGGACCTGTG GGGAGATGTC ATCCATGTCA ACGGACAGCC ATGGCCTTTC 1020
CTTAACGTCC AGCCCCGCAA GTACCGTTTC CGATTCCTCA ACGCTGCCGT GTCTCGTGCT 1080
TGGCTCCTCT ACCTCGTCAG GACCAGCTCT CCCAACGTCA GAATTCCTTT CCAAGTCATT 1140
GCCTCTGATG CTGGTCTCCT TCAAGCCCCC GTTCAGACCT CTAACCTCTA CCTTGCTGTT 1200
GCCGAGCGTT ACGAGATCAT TATTGGTATG CCCTCCCCTC TCACGAATGA GTCAAGAACT 1260
CTAAGACTAA CACTTGTAGA CTTCACCAAC TTTGCTGGCC AGACTCTTGA CCTGCGCAAC 1320
GTTGCTGAGA CCAACGATGT CGGCGACGAG GATGAGTACG CTCGCACTCT CGAGGTGATG 1380
CGCTTCGTCG TCAGCTCTGG CACTGTTGAG GACAACAGCC AGGTCCCCTC CACTCTCCGT 1440
GACGTTCCTT TCCCTCCTCA CAAGGAAGGC CCCGCCGACA AGCACTTCAA GTTTGAACGC 1500
AGCAACGGAC ACTACCTGAT CAACGATGTT GGCTTTGCCG ATGTCAATGA GCGTGTCCTG 1560
GCCAAGCCCG AGCTCGGCAC CGTTGAGGTC TGGGAGCTCG AGAACTCCTC TGGAGGCTGG 1620
AGCCACCCCG TCCACATTCA CCTTGTTGAC TTCAAGATCC TCAAGCGAAC TGGTGGTCGT 1680
GGCCAGGTCA TGCCCTACGA GTCTGCTGGT CTTAAGGATG TCGTCTGGTT GGGCAGGGGT 1740
GAGACCCTGA CCATCGAGGC CCACTACCAA CCCTGGACTG GAGCTTACAT GTGGCACTGT 1800
CACAACCTCA TTCACGAGGA TAACGACATG ATGGCTGTAT TCAACGTCAC CGCCATGGAG 1860
GAGAAGGGAT ATCTTCAGGA GGACTTCGAG GACCCCATGA ACCCCAAGTG GCGCGCCGTT 1920
CCTTACAACC GCAACGACTT CCATGCTCGC GCTGGAAACT TCTCCGCCGA GTCCATCACT 1980
GCCCGAGTGC AGGAGCTGGC CGAGCAGGAG CCGTACAACC GCCTCGATGA GATCCTGGAG 2040
GATCTTGGAA TCGAGGAGTA GTCTAGA                                    2067
```

Figure 5

PHENOL OXIDIZING ENZYMES

This application is a continuation application of application Ser. No. 10/080,233 filed Feb. 19, 2002, now abandoned, which is a continuation application of application Ser. No. 09/218,702, filed Dec. 22, 1998, now U. S. Pat. No. 6,426,410.

FIELD OF THE INVENTION

The present invention relates to novel phenol oxidizing enzymes, in particular, novel phenol oxidizing enzymes derived from strains of *Stachybotrys* and novel strains of the genus *Stachybotrys* producing these enzymes. The present invention provides methods and host cells for expressing *Stachybotrys* phenol oxidizing enzymes as well as methods for producing expression systems.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to $H_2O$. While being capable of using a wide variety of different phenolic compounds as electron donors, phenol oxidizing enzymes are very specific for molecular oxygen as the electron acceptor.

Phenol oxidizing enzymes can be utilized for a wide variety of applications, including the detergent industry, the paper and pulp industry, the textile industry and the food industry. In the detergent industry, phenol oxidizing enzymes have been used for preventing the transfer of dyes in solution from one textile to another during detergent washing, an application commonly referred to as dye transfer inhibition.

Most phenol oxidizing enzymes exhibit pH optima in the acidic pH range while being inactive in neutral or alkaline pHs.

Phenol oxidizing enzymes are known to be produced by a wide variety of fungi, including species of the genii *Aspergillus, Neurospora, Podospora, Botytis, Pleurotus, Fomes, Phlebia, Trametes, Polyporus, Rhizoctonia* and *Lentinus*. However, there remains a need to identify and isolate phenol oxidizing enzymes, and organisms capable of naturally-producing phenol oxidizing enzymes, which present pH optima in the alkaline range for use in detergent washing methods and compositions.

SUMMARY OF THE INVENTION

The present invention relates to novel phenol oxidizing enzymes obtainable from *Stachybotrys*. In particular, the enzymes of the present invention are capable of modifying the color associated with dyes and colored compounds having different chemical structures, especially at neutral or alkaline pH. Based on their color modifying ability, phenol oxidizing enzymes of the present invention can be used, for example, for pulp and paper bleaching, for bleaching the color of stains on fabric and for anti-dye transfer in detergent and textile applications. In one aspect of the present invention, the phenol oxidizing enzyme is able to modify the color in the absence of an enhancer. In another aspect of the present invention, the phenol oxidizing enzyme is able to modify the color in the presence of an enhancer.

The present invention is based upon the identification and characterization of a polynucleotide sequence (SEQ ID NO:1) encoding a phenol oxidizing enzyme obtainable from *Stachybotrys* and having the deduced amino acid sequence as shown in SEQ ID NO:2. The *Stachybotrys* genomic sequence is provided in SEQ ID NO:3. Accordingly, the present invention provides phenol oxidizing enzymes obtainable from *Stachybotrys* and comprising at least 65% identity, at least 70%, at least 75% identity, at least 80% identity, at least 85% identity, at least 90% identity and at least 95% identity to the phenol oxidizing enzyme having the amino acid sequence disclosed in SEQ ID NO:2 as long as the enzyme is capable of modifying the color associated with dyes or colored compounds. In one embodiment, the phenol oxidizing enzyme has the amino acid sequence as shown in SEQ ID NO:2.

In another embodiment, the phenol oxidizing enzyme is obtainable from a *Stachybotrys* species including *Stachybotrys parvispora, Stachybotrys chartarum; S. kampalensis; S. theobromae; S. bisbyi, S. cylindrospora, S. dichroa, S. oenanthes* and *S. nilagerica*. In a preferred embodiment, the *Stachybotrys* includes *Stachybotrys chartarum* MUCL 38898 and *S. chartarum* MUCL 30782.

In yet another embodiment, the present invention provides an isolated polynucleotide encoding a phenol oxidizing enzyme obtainable from *Stachybotrys* wherein said polynucleotide comprises a nucleic acid sequence having at least 65% identity, at least 70%, at least 75% identity, at least 80%, at least 85%, at least 90% and at least 95% identity to SEQ ID NO:1 as long as the polynucleotide encodes a phenol oxidizing enzyme capable of modifying the color associated with dyes or colored compounds. The present invention also encompasses polynucleotide sequences that hybridize under conditions of high stringency to the polynucleotide shown in SEQ ID NO:1 or SEQ ID NO:3. The present invention also provides polynucleotides that encode the amino acid sequence as shown in SEQ ID NO:2. In a preferred embodiment, the polynucleotide has the nucleic acid sequence as shown in SEQ ID NO:1 or SEQ ID NO:3. The present invention also provides expression vectors and host cells comprising polynucleotides of the present invention.

The present invention additionally relates to methods for producing a phenol oxidizing enzyme obtainable from *Stachybotrys*. Accordingly, the present invention provides a method for producing said enzyme comprising the steps of obtaining a host cell comprising a polynucleotide encoding said phenol oxidizing enzyme obtainable from *Stachybotrys* wherein said enzyme has at least 65% identity to the amino acid sequence disclosed in SEQ ID NO:2; growing said host cell under conditions suitable for the production of said phenol oxidizing enzyme; and optionally recovering said phenol oxidizing enzyme produced. In one embodiment, the polynucleotide comprises the sequence as shown in SEQ ID NO:1. In another embodiment, the polynucleotide comprises the sequence as shown in SEQ ID NO: 3.

The present invention also provides a method for producing a host cell comprising a polynucleotide encoding a phenol oxidizing enzyme of the present invention comprising the steps of obtaining a polynucleotide encoding said phenol oxidizing enzyme obtainable from *Stachybotrys* and having at least 65% identity to the amino acid sequence disclosed in SEQ ID NO:2; introducing said polynucleotide into said host cell; and growing said host cell under conditions suitable for the production of said phenol oxidizing enzyme. In another embodiment, the polynucleotide comprises the sequence as shown in SEQ ID NO: 3.

In one aspect of the present invention, the host cell comprising a polynucleotide encoding a phenol oxidizing enzyme includes filamentous fungus, yeast and bacteria. In one embodiment, the host cell is a filamentous fungus including *Aspergillus* species, *Trichoderma* species and *Mucor* species. In a preferred embodiment, the filamentous fungus host cell includes *Aspergillus niger* var. *awamori* and *Trichoderma reseei.*

In another embodiment of the present invention, the host cell is a yeast which includes *Saccharomyces, Pichia, Hansenula, Schizosaccharomyces, Kluyveromyces* and *Yarrowia* species. In yet a another embodiment, the *Saccharomyces* species is *Saccharomyces cerevisiae*. In an additional embodiment, the host cell is a gram positive bacteria, such as a *Bacillus* species, or a gram negative bacteria, such as an *Escherichia* species.

Also provided herein are detergent compositions comprising the amino acid having at least 65% identity, at least 70%, at least 75% identity, at least 80% identity, at least 85% identity, at least 90% identity and at least 95% identity to the phenol oxidizing enzyme having the amino acid sequence disclosed in SEQ ID NO:2 as long as the enzyme is capable of modifying the color associated with dyes or colored compounds. In a preferred embodiment, the amino acid has the sequence as shown in SEQ ID NO: 2

The present invention also encompasses methods for modifying the color associated with dyes or colored compounds which occur in stains on fabric, comprising the steps of contacting the fabric with a composition comprising an amino acid sequence having at least 65% identity, at least 70%, at least 75% identity, at least 80% identity, at least 85% identity, at least 90% identity and at least 95% identity to the phenol oxidizing enzyme having the amino acid sequence disclosed in SEQ ID NO:2 as long as the enzyme is capable of modifying the color associated with dyes or colored compounds. In a preferred embodiment of the method, the amino acid has the sequence as shown in SEQ ID NO:2. In one aspect of the method, the pH optimum is between 5.0 and 11.0, in another aspect, the pH optimum is between 7 and 10.5 and in yet another aspect the pH optimum is between 8.0 and 10. In a further aspect of the method, the optimum temperature is between 20 and 60 degrees C. and in another aspect between 20 and 40 degrees C. The present invention also provides methods for preventing dye transfer in detergent and textile applications.

BRIEF DESCRIPTION OF THE DRAWINGS

FIG. 1 illustrates the nucleic acid (SEQ ID NO:1) and amino acid (SEQ ID NO:2) sequence for a phenol oxidizing enzyme obtainable from *Stachybotrys chartarum.*

FIG. 2 illustrates the genomic sequence (SEQ ID NO:3) for a phenol oxidizing enzyme obtainable from *Stachybotrys chartarum.*

FIG. 3 is an amino acid alignment of *Stachybotrys* phenol oxidizing enzyme SEQ ID NO:2 (bottom line) and *Bilirubin* oxidase (SEQ ID NO:4).

FIG. 5 shows the nucleic acid sequence of the PCR generated fragment of *Stachybotrys* described in Example 13 that was expressed in *Aspergillus.*

DETAILED DESCRIPTION

Definitions

Figure 4:
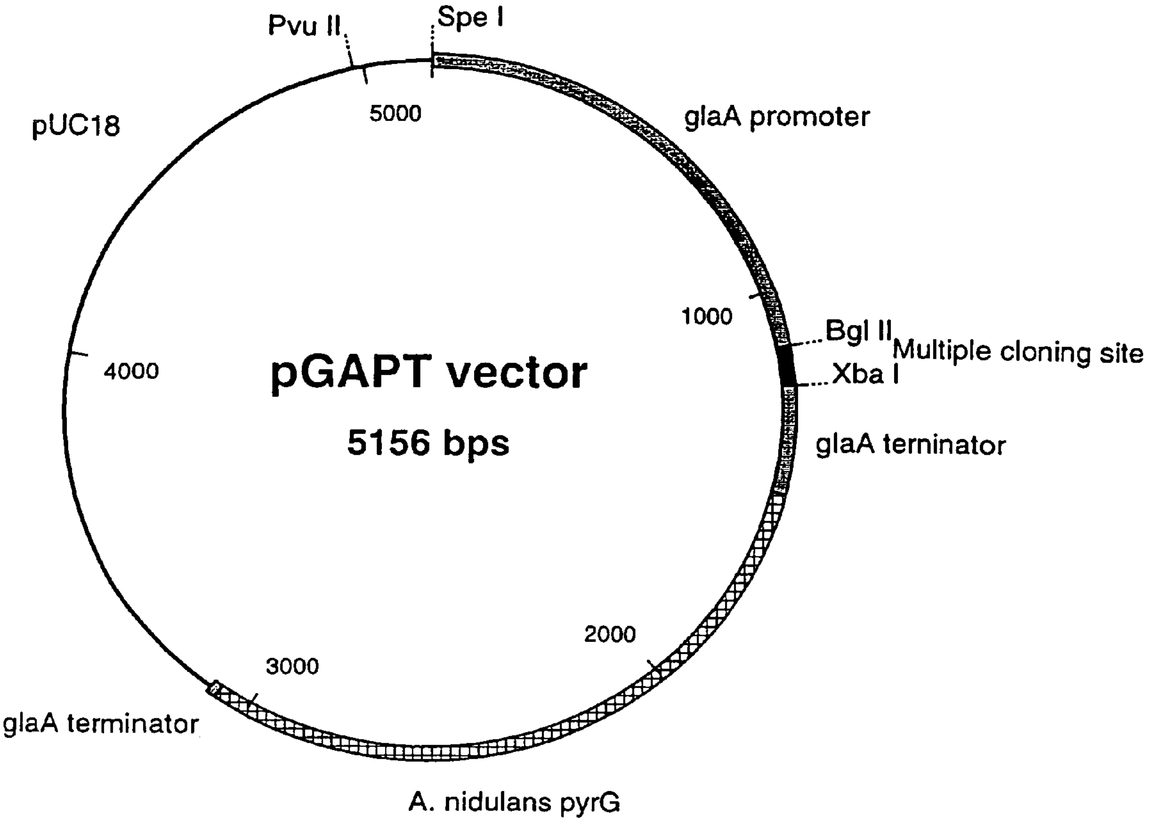
FIG. 4 provides an illustration of the vector pGAPT which was used for the expression of *Stachybotrys* phenol oxidizing enzyme in *Aspergillus*. Base 1 to 1134 contains *Aspergillus niger* glucoamylase gene promoter. Base 1227 to 1485 and 3079 to 3100 contains *Aspergillus niger* glucoamylase terminator. *Aspergillus nidulans* pyrG gene was inserted from 1486 to 3078 as a marker for fungal transformation. The rest of the plasmid contains pUC18 sequences for propagation in *E. coli*. Nucleic acid encoding the *Stachybotrys* phenol oxidizing enzyme of SEQ ID NO:1 was cloned into the Bgl II and Xba I restriction sites.

As used herein, the term phenol oxidizing enzyme refers to those enzymes which catalyze redox reactions and are specific for molecular oxygen and hydrogen peroxide as the electron acceptor. When *Stachybotrys* phenol oxidizing enzymes purified by the method disclosed in Examples 4 and 5 are boiled and subjected to SDS gel electrophoresis, three molecular weight species are observed. As used herein, the term “enzyme” encompasses any molecular weight species which alone or in combination with at least one other molecular weight species is able to modify the color associated with a dye or colored compound. One phenol oxidizing enzyme of the present invention obtainable from *Stachybotrys chartarum* is shown in SEQ ID NO:2.

As used herein, *Stachybotrys* refers to any *Stachybotrys* species which produces a phenol oxidizing enzyme capable of modifying the color associated with dyes or colored compounds. The present invention encompasses derivatives of natural isolates of *Stachybotrys*, including progeny and mutants, as long as the derivative is able to produce a phenol oxidizing enzyme capable of modifying the color associated with dye or color compounds.

As used herein in referring to phenol oxidizing enzymes, the term “obtainable from” means phenol oxidizing enzymes equivalent to those that originate from or are naturally-produced by the particular microbial strain mentioned. To exemplify, phenol oxidizing enzymes obtainable from *Stachybotrys* refer to those phenol oxidizing enzymes which are naturally-produced by *Stachybotrys*. The present invention encompasses phenol oxidizing enzymes identical to those produced by *Stachybotrys* species but which through the use of genetic engineering techniques are produced by non-*Stachybotrys* organisms transformed with a gene encoding said phenol oxidizing enzyme and those produced by other organisms which are identical or equivalent to those from *Stachybotrys*. Being equivalent means that the phenol oxidizing enzyme is encoded by a polynucleotide capable of hybridizing to the polynucleotide having the sequence as shown in SEQ ID NO:1 or SEQ ID NO:3 under conditions of intermediate to maximum stringency. Being equivalent means that the phenol oxidizing enzyme comprises at least 65% identity, at least 70%, at least 75% identity, at least 80% identity, at least 85% identity, at least 90% identity or at least 95% identity to the phenol oxidizing enzyme having the amino acid sequence disclosed in SEQ ID NO:2. Percent identity at the nucleic acid level is determined using the FastA program and percent identity at the amino acid level is determined using the TFastA both of which use the method of Pearson and Lipman (PNAS USA, 1988, 85:2444–2448). The present invention also encompasses mutants, variants and derivatives of the phenol oxidizing enzymes of the present invention as long as the mutant, variant or derivative phenol oxidizing enzyme is able to retain at least one characteristic activity of the naturally occurring phenol oxidizing enzyme.

As used herein, the term ‘colored compound’ refers to a substance that adds color to textiles or to substances which result in the visual appearance of stains. As defined in Dictionary of Fiber and Textile Technology (Hoechst Celanese Corporation (1990) PO Box 32414, Charlotte N.C. 28232), a dye is a colored compound that is incorporated into the fiber by chemical reaction, absorption, or dispersion. Examples of dyes include direct Blue dyes, acid Blue dyes, direct red dyes, reactive Blue and reactive Black dyes. A catalogue of commonly used textile dyes is found in Colour Index, $3^{rd}$ ed. Vol. 1–8. Examples of substances which result in the visual appearance of stains are polyphenols, carotenoids, anthocyanins, tannins, Maillard reaction products, etc.

As used herein the phrase "modify the color associated with a dye or colored compound" or "modification of the colored compound" means that the dye or compound is changed through oxidation such that either the color appears modified, i.e., the color visually appears to be decreased, lessened, decolored, bleached or removed, or the color is not affected but the compound is modified such that dye redeposition is inhibited. The present invention encompasses the modification of the color by any means including, for example, the complete removal of the colored compound from stain on a fabric by any means as well as a reduction of the color intensity or a change in the color of the compound.

The "anti-dye transfer" or "anti-dye redeposition" effect may be a function of the color modification activity of a phenol oxidizing compound, i.e., soluble dyes or colored components are oxidized or bleached and are not able to be redeposited as a color on the fabric, or a function of substrate modification in the absence of color modification such that a dye or colored component becomes water soluble and is rinsed away. The ability of a phenol oxidizing compound used alone or together with an enhancer to oxidize an soluble or dispersed dye or colored compound to a colorless species in a wash solution prevents the color redeposition effect.

As used herein, the term "mutants and variants", when referring to phenol oxidizing enzymes, refers to phenol oxidizing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phenol oxidizing enzyme. The term phenol oxidizing enzyme "derivative" as used herein refers to a portion or fragment of the full-length naturally occurring or variant phenol oxidizing enzyme amino acid sequence that retains at least one activity of the naturally occurring phenol oxidizing enzyme. As used herein, the term "mutants and variants", when referring to microbial strains, refers to cells that are changed from a natural isolate in some form, for example, having altered DNA nucleotide sequence of, for example, the structural gene coding for the phenol oxidizing enzyme; alterations to a natural isolate in order to enhance phenol oxidizing enzyme production; or other changes that effect phenol oxidizing enzyme expression.

The term "enhancer" or "mediator" refers to any compound that is able to modify the color associated with a dye or colored compound in association with a phenol oxidizing enzyme or a compound which increases the oxidative activity of the phenol oxidizing enzyme. The enhancing agent is typically an organic compound.

Phenol Oxidizing Enzymes

The phenol oxidizing enzymes of the present invention function by catalyzing redox reactions, i.e., the transfer of electrons from an electron donor (usually a phenolic compound) to molecular oxygen (which acts as an electron acceptor) which is reduced to water. Examples of such enzymes are laccases (EC 1.10.3.2), bilirubin oxidases (EC 1.3.3.5), phenol oxidases (EC 1.14.18.1), catechol oxidases (EC 1.10.3.1).

The present invention encompasses *Stachybotrys* phenol oxidizing enzymes. comprising at least 65% identity, at least 70%, at least 75% identity, at least 80% identity, at least 85% identity, at least 90% identity or at least 95% identity to the phenol oxidizing enzyme having the amino acid sequence disclosed in SEQ ID NO:2.

Nucleic Acid Encoding Phenol Oxidizing Enzymes

The present invention encompasses polynucleotides which encode phenol oxidizing enzymes obtainable from *Stachybotrys* species which polynucleotides comprise at least 65% identity, at least 70% identity, at least 75% identity, at least 80% identity, at least 85% identity, at least 90% identity and at least 95% identity to the polynucleotide sequence disclosed in SEQ ID NO:1 as long as the enzyme encoded by the polynucleotide is capable of modifying the color associated with dyes or colored compounds. In a preferred embodiment, the phenol oxidizing enzyme has the polynucleotide sequence as shown in SEQ ID NO:1. As will be understood by the skilled artisan, due to the degeneracy of the genetic code, a variety of polynucleotides can encode the phenol oxidizing enzyme disclosed in SEQ ID NO: 2. The present invention encompasses all such polynucleotides.

The nucleic acid encoding a phenol oxidizing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a *Stachybotrys* species (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Nucleic acid sequences derived from genomic DNA may contain regulatory regions in addition to coding regions. Whatever the source, the isolated nucleic acid encoding a phenol oxidizing enzyme of the present invention should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid fragments are generated, identification of the specific DNA fragment encoding a phenol oxidizing enzyme may be accomplished in a number of ways. For example, a phenol oxidizing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

The present invention encompasses phenol oxidizing enzymes obtainable from *Stachybotrys* species which are identified through nucleic acid hybridization techniques using SEQ ID NO:1 as a probe or primer and screening nucleic acid of either genomic of cDNA origin. Nucleic acid encoding phenol oxidizing enzymes obtainable from *Stachybotrys* species and having at least 65% identity to SEQ ID NO:1 can be detected by DNA-DNA or DNA-RNA hybridization or amplification using probes, portions or fragments of SEQ ID NO:1. Accordingly, the present invention provides a method for the detection of nucleic acid encoding a phenol oxidizing enzyme encompassed by the present invention which comprises hybridizing part or all of a nucleic acid sequence of SEQ ID NO:1 with *Stachybotrys* nucleic acid of either genomic or cDNA origin.

Also included within the scope of the present invention are polynucleotide sequences that are capable of hybridizing to the nucleotide sequence disclosed in SEQ ID NO:1 under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined "stringency" as explained below.

"Maximum stringency" typically occurs at about Tm−5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from SEQ ID NO:1 preferably about 12 to 30 nucleotides, and more preferably about 25 nucleotides can be used as a probe or PCR primer.

A preferred method of isolating a nucleic acid construct of the invention from a cDNA or genomic library is by use of polymerase chain reaction (PCR) using degenerate oligonucleotide probes prepared on the basis of the amino acid sequence of the protein having the amino acid sequence as shown in SEQ ID NO:2. For instance, the PCR may be carried out using the techniques described in U.S. Pat. No. 4,683,202. PCR Expression Systems The present invention provides host cells, expression methods and systems for the production of phenol oxidizing enzymes obtainable from *Stachybotrys* species in host microorganisms, such as fungus, yeast and bacteria. Once nucleic acid encoding a phenol oxidizing enzyme of the present invention is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding phenol oxidizing enzymes obtainable from *Stachybotrys* species and having at least 65%, at least 70%, at least 75%, at least 80%, at least 85%, at least 90% and at least 95% identity to the nucleic acid of SEQ ID NO:1 is obtained and transformed into a host cell using appropriate vectors. A variety of vectors and transformation and expression cassettes suitable for the cloning, transformation and expression in fungus, yeast and bacteria are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phenol oxidizing enzymes in a host cell are known to those skilled in the art. Virtually any promoter capable of driving these phenol oxidizing enzyme is suitable for the present invention. Nucleic acid encoding the phenol oxidizing enzyme is linked operably through initiation codons to selected expression control regions for effective expression of the oxidative or reducing enzymes. Once suitable cassettes are constructed they are used to transform the host cell.

General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation. For *Aspergillus* and *Trichoderma*, PEG and Calcium mediated protoplast transformation can be used (Finkelstein, D B 1992 Transformation. In Biotechnology of Filamentous Fungi. Technology and Products (eds by Finkelstein & Bill) 113–156. Electroporation of protoplast is disclosed in Finkelstein, D B 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia. FEMS Microbiology Letters 125 293–298. Agrobacterium mediated transformation is disclosed in Groot et al. (1998) Agrobacterium tumefaciens-mediated transformation of filamentous fungi. Nature Biotechnology 16 839–842. For transformation of *Saccharomyces*, lithium acetate mediated transformation and PEG and calcium mediated protoplast transformation as well as electroporation techniques are known by those of skill in the art.

Host cells which contain the coding sequence for a phenol oxidizing enzyme of the present invention and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

As described herein, the genomic sequence (SEQ ID NO:3) encoding phenol oxidizing enzyme obtainable from *Stachybotrys chartarum* (MUCL 38898) was isolated and expressed in *Aspergillus niger* var. *awamori* and *Tricho-*

*derma reesei*. The cDNA (SEQ ID NO: 1) obtainable from *Stachybotrys chartarum* (MUCL 38898) was isolated and expressed in *Saccharomyces cerevisiae*.

Phenol Oxidizing Enzyme Activities

The phenol oxidizing enzymes of the present invention are capable of using a wide variety of different phenolic compounds as electron donors, while being very specific for molecular oxygen as the electron acceptor.

Depending upon the specific substrate and reaction conditions, e.g., temperature, presence or absence of enhancers, etc., each phenol oxidizing enzyme oxidation reaction will have an optimum pH. For example, the *Stachybotrys parvispora* phenol oxidizing enzyme produced as described in Example 4 has a pH optimum of from about 5.0 to about 7.0, as determined by incubation for 2 minutes at 20 degrees C. with ABTS as substrate; a pH optimum of from about 6.0 to about 7.5, as determined by incubation for 2 minutes at 20 degrees C. with syringaldizin as substrate; and a pH optimum of from about 7.0 to about 9.0, as determined by incubation for 2 minutes at 20 degrees C. with 2,6-dimethoxyphenol as substrate, and which is able to oxidize guiacol.

Phenol oxidizing enzyme obtained from *Stachybotrys chartarum* MUCL 38898 and produced as described in Examples 4 and 5 has a pH optimum of about 8.0 at both 20 and 40 degrees C. as determined by incubation with DMP as a substrate and in the presence of a total of 17.2 μg enzyme and a pH optimum of about 5.0 to 7.0 as determined by incubation with ABTS as a substrate and in the presence of a total of 1.7 μg enzyme.

A particularly important characteristic of the phenol oxidizing enzymes is their expression of high levels of enzymatic activity, at about 20–40 degrees C., in a broad range of pHs, including a broad range of neutral to alkaline pHs. In particular is their ability to express high levels of enzymatic activity in the pH range of from about 7.0 to about 10.5 in temperatures of about 20–35 degrees C.

Applications of Polyphenol Oxidizing Enzymes

As described infra, the *Stachybotrys* phenol oxidizing enzymes of the present invention are capable of oxidizing a wide variety of dyes or colored compounds having different chemical structures, using oxygen or hydrogen peroxide as the electron acceptor. Accordingly phenol oxidizing enzymes of the present invention are used in applications where it is desirable to modify the color associated with dyes or colored compounds, such as in cleaning, for removing the food stains on fabric and anti-dye redeposition; textiles; and paper and pulp applications.

Colored Compounds

In the present invention, a variety of colored compounds could be targets for oxidation by phenol oxidizing enzymes of the present invention. For example, in detergent applications, colored substances which may occur as stains on fabrics can be a target. Several types or classes of colored substances may appear as stains, such as porphyrin derived structures, such as heme in blood stain or chlorophyll in plants; tannins and polyphenols (see P. Ribéreau-Gayon, Plant Phenolics, Ed. Oliver & Boyd, Edinburgh, 1972, pp. 169–198) which occur in tea stains, wine stains, banana stains, peach stains; carotenoids, the coloured substances which occur in tomato (lycopene, red), mango (carotene, orange-yellow) (G. E. Bartley et al., The Plant Cell (1995), Vol 7, 1027–1038); anthocyanins, the highly colored molecules which occur in many fruits and flowers (P. Ribéreau-Gayon, Plant Phenolics, Ed. Oliver & Boyd, Edinburgh, 1972, 135–169); and Maillard reaction products, the yellow/brown colored substances which appear upon heating of mixtures of carbohydrate molecules in the presence of protein/peptide structures, such as found in cooking oil.

Enhancers

A phenol oxidizing enzyme of the present invention can act to modify the color associated with dyes or colored compounds in the presence or absence of enhancers depending upon the characteristics of the compound. If a compound is able to act as a direct substrate for the phenol oxidizing enzyme, the phenol oxidizing enzyme can modify the color associated with a dye or colored compound in the absence of an enhancer, although an enhancer may still be preferred for optimum phenol oxidizing enzyme activity. For other colored compounds unable to act as a direct substrate for the phenol oxidizing enzyme or not directly accessible to the phenol oxidizing enzyme, an enhancer is required for optimum phenol oxidizing enzyme activity and modification of the color.

Enhancers are described in for example WO 95/01426 published 12 Jan. 1995; WO 96/06930, published 7 Mar. 1996; and WO 97/11217 published 27 Mar. 1997. Enhancers include but are not limited to phenothiazine-10-propionic acid (PTP), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis (3-ethylbenzothiazoline-6-sulfonate (ABTS).

Cultures

The present invention encompasses *Stachybotrys* strains and natural isolates, and derivatives of such strains and isolates, such as strains of the species *Stachybotrys parvispora*, including, in particular, *Stachybotrys parvispora* var. *hughes* MUCL 38996; strains of the species *Stachybotrys chartarum* including, in particular, *Stachybotrys chartarum* MUCL 38898*; S. parvispora* MUCL 9485*; S. chartarum* MUCL 30782*; S. kampalensis* MUCL 39090*; S. theobromae* MUCL 39293; and strains of the species *S. bisbyi, S. cylindrospora, S. dichroa, S. oenanthes* and *S. nilagerica* which produce phenol oxidizing enzymes of the present invention.

The present invention provides substantially biologically-pure cultures of novel strains of the genus *Stachybotrys*, and, in particular substantially biologically-pure cultures of the strains *Stachybotrys parvispora* MUCL 38996 and *Stachybotrys chartarum* MUCL 38898 from which phenol oxidizing enzymes can be purified.

Purification

The phenol oxidizing enzymes of the present invention may be produced by cultivation of phenol oxidizing enzyme-producing *Stachybotrys* strains (such as *S. parvispora* MUCL 38996, *S. chartarum* MUCL 38898) under aerobic conditions in nutrient medium containing assimiable carbon and nitrogen together with other essential nutrient(s). The medium can be composed in accordance with principles well-known in the art.

During cultivation, the phenol oxidizing enzyme-producing strains secrete phenol oxidizing enzyme extracellularly. This permits the isolation and purification (recovery) of the phenol oxidizing enzyme to be achieved by, for example, separation of cell mass from a culture broth (e.g. by filtration or centrifugation). The resulting cell-free culture broth can be used as such or, if desired, may first be concentrated (e.g. by evaporation or ultrafiltration). If desired, the phenol oxidizing enzyme can then be separated from the cell-free broth and purified to the desired degree by conventional methods, e.g. by column chromatography, or even crystallized.

The phenol oxidizing enzymes of the present invention may be isolated and purified from the culture broth into which they are extracellularly secreted by concentration of the supernatant of the host culture, followed by ammonium sulfate fractionation and gel permeation chromatography.

The phenol oxidizing enzymes of the present invention may be formulated and utilized according to their intended application. In this respect, if being used in a detergent composition, the phenol oxidizing enzyme may be formulated, directly from the fermentation broth, as a coated solid using the procedure described in U.S. Pat. No. 4,689,297. Furthermore, if desired, the phenol oxidizing enzyme may be formulated in a liquid form with a suitable carrier. The phenol oxidizing enzyme may also be immobilized, if desired.

The present invention also encompasses expression vectors and recombinant host cells comprising a *Stachybotrys* phenol oxidizing enzyme of the present invention and the subsequent purification of the phenol oxidizing enzyme from the recombinant host cell.

Detergent Compositions

A *Stachybotrys* phenol oxidizing enzyme of the present invention may be used in detergent or cleaning compositions. Such compositions may comprise, in addition to the phenol oxidizing enzyme, conventional detergent ingredients such as surfactants, builders and further enzymes such as, for example, proteases, amylases, lipases, cutinases, cellulases or peroxidases. Other ingredients include enhancers, stabilizing agents, bactericides, optical brighteners and perfumes. The detergent compositions may take any suitable physical form, such as a powder, an aqueous or non aqueous liquid, a paste or a gel. Examples of detergent compositions are given in WO 95/01426, published 12 Jan. 1995 and WO 96/06930 published 7 Mar. 1996.

Having thus described the phenol oxidizing enzymes of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of per cent weight per volume (w/v). As used herein, dilutions, quantities, etc., which are expressed in terms of % (v/v), refer to percentage in terms of volume per volume. Temperatures referred to herein are given in degrees centigrade (C.). The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLE 1

Isolation and Identification of *Stachybotrys parvispora* var. *hughes* Strain A new strain of the species *Stachybotrys parvispora* var. *hughes* was isolated from soil samples on an agar-agar nutrient medium and selected by its production of an enzyme having oxidase activity.

The new strain was individually cultured on corn meal agar (DIFCO) at 25 degrees C. for a period of three weeks.

The new strain of *S. parvispora* was identified by its slow growth in corn meal agar at 25 degrees C., being less than 4 cm in three weeks, its formation of conidia and the morphological characteristics of the formed conidia.

After growth for three days on corn meal agar at 25 degrees C., microscopic observation revealed that the cells of the new strain of *S. parvispora* have the form of conidia of 5.25×3.75–4.5 mm in size which are coarsely roughened and are gathered in a dark olive gray mucilaginous drop, borne from phialides 9–11×3.5–4.5 mm clustered in verticille. *Conidiophores* are smooth-walled, up to 200 mm long (see Jong, S. C and E. E. Davis, Mycotaxon 3:409–485.).

The new strain of *S. parvispora* so identified was deposited under the provisions of the Treaty of Budapest in the Belgian Coordinated Collections of Microorganisms, Mycothâque de I'Universitã Catholique de Louvain (MUCL), Place Croix du Sud 3, Louvain-La-Neuve, Belgium B-1348 on 5 Dec. 1995 and given accession number MUCL 38996.

EXAMPLE 2

Isolation and Identification of *Stachybotrys chartarum* Strain

A new strain of the species *Stachybotrys chartarum* (formerly named *Stachybotrys* atra var. *corda*) was isolated from soil samples on an agar-agar nutrient medium and selected by its production of an enzyme having oxidase activity.

The new strain was individually cultured on corn meal agar (DIFCO) at 25 degrees C. for a period of three weeks.

The new strain *S. chartarum* was identified by its rapid growth on corn meal agar at 25 degrees C., being more than 4 cm in three weeks, its formation of conidia and the morphological characteristics of the formed conidia.

After growth for three days on corn meal agar at 25 degrees C., microscopic observation revealed that the cells of the new strain of *S. chartarum* have the form of conidia of 8–11×5–10 mm in size which are coarsely roughened and are gathered in a dark olive gray mucilaginous drop, borne from phialides 10–13×4–6 mm clustered in verticille. *Conidiophores* are smooth-walled, up to 1000 mm long (see Jong, S. C and E. E. Davis, Mycotaxon 3:409–485).

The new strain of *S. chartarum* so identified was deposited under the provisions of the Treaty of Budapest in the Belgian Coordinated Collections of Microorganisms, Mycothâque de I'Universitã Catholique de Louvain (MUCL), Place Croix du Sud 3, Louvain-La-Neuve, Belgium B-1348 on 5 Dec. 1995 and given accession number MUCL 38898.

EXAMPLE 3

Preparation of Conidial Stock Suspension for Inoculation

*Stachybotrys parvispora* MUCL 38996, obtained as described above in Example 1, was isolated on PDA (potato dextrose agar) plates (DIFCO).

One colony was suspended in 5 ml of 0.9% (w/v) NaCl, containing about 30 sterile glass beads (diameter 5 mm). The suspension was thoroughly agitated in a vortex mixer (BENDER & HOBEIN AG), until complete homogenization of the mycelium was obtained (full speed for approximately 15–20 minutes). Several dilutions (ranging from $10^{-5}$ to $10^{-7}$) of this homogenate were then plated on respective sterile PDA plates and incubated at 30 degrees C. for about 5 weeks to allow formation of conidia (dark-brownish in color).

Three plates, each containing approximately 50 isolated sporulated colonies (as evidenced by their dark-brownish color) were then spread with 5 ml of 0.9% (w/v) NaCl and scraped with a glass rod to suspend the conidia. The resulting suspensions were pooled and filtered using Miracloth (CALBIOCHEM) membrane in order to remove the remaining mycelium. The result were conidial stock suspensions.

The titer (measured in terms of colony forming units (cfu) per ml) of the resulting suspension was then determined by plating dilutions [in 0.9% (w/v) NaCl] on PDA plates. The titers of the resulting conidial stock suspensions ranged from $10^6$ to $10^7$ cfu/ml.

EXAMPLE 4

Production of Phenol Oxidizing Enzyme

Production of Enzyme from *Stachybotrys parvispora*

A twenty liter fermentor containing glucose and potato extract was prepared by boiling 4.5 kilograms of peeled and diced potatoes for 30 minutes in 15 liters of water (milli-Q quality), filtering the resulting suspension through hydrophilic cotton gauze (STELLA), collecting the resulting filtrate and then supplementing the collected filtrate with 300 grams of glucose. The glucose supplemented filtrate was then placed in the fermentor and sterilized for 30 minutes at 120° C. The sterilized supplemented filtrate had a pH of 5.8.

The twenty liter fermentor was then inoculated with 15 ml of the conidial stock suspension, obtained as described above in Example 3, and fermentation was conducted for 144 hours at 37 degrees C.

Fermentation was performed under a constant air flow of 4.5 liters/minute and a constant agitation of 100 RPM (revolutions per minute) (diameter 13 cm) without pH control.

An approximately 50 ml sample of the culture (fermentation) broth was then withdrawn from the fermentor and centrifuged at 12,000 g for 5 minutes. The supernatant was then removed from the pellet.

The presence of phenol oxidizing enzyme activity in the supernatant was then measured using the following standard assay procedure, based on the oxidation of ABTS [2,2'-azino-bis-(3-ethylbenzothiazoline-6-sulfonate)] by oxygen: a final reaction volume of 1 ml containing Tris[Tris(hydroxymethyl)-aminomethane]/HCl 200 mM (pH 7.0), 0.9 mM ABTS (Diammonium salt from SIGMA) and an appropriate amount of the preparation to be assayed (which, in this example, is the supernatant diluted with water as described below) was prepared. The assay reaction was started by the addition of the preparation to be assayed (which in this example is the supernatant dilution) to form the final 1 ml reaction volume. The greenish-blue color produced by the oxidation of ABTS was then continually measured by recording the optical density (OD) at 420 nm during two minutes, using a spectrophotometer (Ultraspec Plus from Pharmacia). The rate of increase of the optical density per minute (ΔOD/minute) was then calculated from the linear part of the curve during 1 minute.

The appropriate amount of the (enzyme) preparation submitted to this standard assay, was adjusted by-dilution with water in order to obtain a ΔOD/minute ranging from 0.2 to 1.0 during the assay.

As used herein, one standard ABTS enzyme unit (hereinafter referred to as one enzyme unit or EU) is defined as the amount of enzyme that produces an increase of one $OD^{420}$ per minute, under these specific conditions.

In this manner, an enzyme activity of 30 EU/ml of culture supernatant was measured.

*Stachybotrys chartarum* Phenol Oxidizing Enzyme Production

*Stachybotrys chartarum* was grown on PDA plates (Difco) for about 5–10 days. A portion of the plate culture (about ¾×¾ inch) was used to inoculate 100 ml of PDB (potato dextrose broth) in 500-ml shake flask. The flask was incubated at 26–28 degrees C., 150 rpm, for 3–5 days until good growth was obtained.

The broth culture was then inoculated into 1 L of PDB in a 2.8-L shake flask. The flask was incubated at 26–28 degrees C., 150 rpm, for 2–4 days until good growth was obtained.

A 10-L fermentor containing a production medium was prepared (containing in grams/liter the following components: glucose 15; lecithin 1.51; t-aconitic acid 1.73; $KH_2PO_4$ 3; $MgSO_4.7H_2O$ 0.8; $CaCl_2.2H_2O$ 0.1; ammonium tartrate 1.2; soy peptone 5; Staley 7359; benzyl alcohol 1; tween 20 1; nitrilotriacetic acid 0.15; $MnSO_4.7H_2O$ 0.05; NaCl 0.1; $FeSO_4.7H_2O$ 0.01; $CoSO_4$ 0.01; $CaCl_2.2H_2O$ 0.01; $ZnSO_4.7H_2O$ 0.01; $CuSO_4$ 0.001; $ALK(SO_4)2.12H_2O$ 0.001; $H_3BO_3$ 0.001; $NaMoO_4.2H_2O$ 0.001). The fermentor was then inoculated with the 1-L broth culture, and fermentation was conducted at 28 degrees C. for 60 hours, under a constant air flow of 5.0 liters/minute and a constant agitation of 120 RPM. The pH was maintained at 6.0.

The presence of phenol oxidizing enzyme activity in the supernatant was measured using the following assay procedure, based on the oxidation of ABTS (2,2'-azino-bis-(3-ethylbenzothiazoline-6-sulfonate)) by oxygen. ABTS (SIGMA, 0.2 ml, 4.5 mM $H_2O$) and NaOAc (1.5 ml, 120 mM in $H_2O$, pH 5.0) were mixed in a cuvette. The reaction was started by addition of an appropriate amount of the preparation to be measured (which in this example is the supernatant dilution) to form a final solution of 1.8 ml. The color produced by the oxidation of ABTS was then measured every 2 seconds for total period of 14 seconds by recording the optical density (OD) at 420 nm, using a spectrophotometer. One ABTS unit (one enzyme unit or EACU) in this example is defined as the change in OD measured at 420 per minute/2 (given no dilution to the sample). In this manner a phenol oxidizing enzyme activity of 3.5 EACU/ml of culture supernatant was measured.

EXAMPLE 5

Purification of the Enzyme

The remaining *Stachybotrys parvispora* culture broth, obtained as described above in Example 4, was then withdrawn from the fermentor and centrifuged for 15 minutes at 4,500 g. *Stachybotrys chartarum* is purified in a similar fashion.

The resulting supernatant was then removed from the pellet and concentrated to 0.6 liters by ultrafiltration using a Amicon ultrafiltration unit equipped with a YMI0 membrane having a 10 kD cutoff.

A volume of 1.4 liters of acetone was added to the concentrate and mixed therewith. The resulting mixture was then incubated for two hours at 20–25 degrees C.

Following incubation, the mixture was centrifuged for 30 minutes at 10,000 g and the resulting pellet was removed from the supernatant. The pellet was then resuspended in a final volume of 800 ml of water.

The resulting suspension was then submitted to ammonium sulfate fractionation as follows: crystalline ammonium sulfate was added to the suspension to 40% saturation and the mixture incubated at 4 degrees C. for 16 hours with gentle magnetic stirring. The mixture was then centrifuged at 10,000 g for 30 minutes and the supernatant removed from the centrifugation pellet for further use. Ammonium sulfate was then added to the supernatant to reach 80% saturation, and the mixture incubated at 4 degrees C. for 16 hours with gentle magnetic stirring. The suspension was then centrifuged for 30 minutes at 10,000 g and the resulting pellet was removed from the supernatant. The pellet was then resuspended in 15 ml of water and concentrated to 6 ml by ultrafiltration using a CENTRIPREP 3000 (AMICON).

The phenol oxidizing enzyme activity of the suspension was then measured using the standard assay procedure, based on the oxidation of ABTS by oxygen, as was described above in Example 4 (but with the exception that the preparation being assayed is the resuspended concentration and not the supernatant dilutions). The phenol oxidizing enzyme activity so measured was 5200 EU/ml.

The enzyme was then further purified by gel permeation chromatography. In this regard, a column containing 850 ml of SEPHACRYL S400 HIGH RESOLUTION (PHARMACIA) was equilibrated with a buffer containing 50 mM $KH_2PO_4/K_2HPO_4$ (pH=7.0) and then loaded with the remainder of the 6 ml suspension described above, and eluted with the buffer containing 50 mM $KH_2PO_4/K_2HPO_4$ (pH=7.0), at a flow rate of 1 ml/minute. Respective fractions were then obtained.

The respective fractions containing the highest phenol oxidizing enzyme activities were pooled together, providing a 60 ml suspension containing the purified phenol oxidizing enzyme.

The phenol oxidizing enzyme activity of the suspension was then measured using the standard assay procedure, based on the oxidation of ABTS by oxygen, as was described above in Example 4. The enzyme activity so measured was 390 EU/ml.

This preparation was then used for further characterization of the enzyme, as will be described at length below.

EXAMPLE 6

Amino Acid Sequence Analysis of *Stachybotrys chartarum* Phenol Oxidizing Enzyme

*Stachybotrys chartarum* phenol oxidizing enzyme prepared as disclosed in Example 4 was subjected to SDS polyacrylamide gel electrophoresis and isolated. The isolated fraction was treated with urea and iodoacetamide and digested by the enzyme endoLysC. The fragments resulting from the endoLysC digestion were separated via HPLC (reverse phase monobore C18 column, CH3CN gradient) and collected in a multititer plate. The fractions were analysed by MALDI for mass determination and sequenced via Edman degradation. The following amino acid sequences were determined and are shown in amino terminus to carboxy terminus orientation:

```
N' DYYFPNYQSARLLXYHDHA C'
N' RGQVMPYESAGLK C'
```

EXAMPLE 7

Cloning Genomic Nucleic Acid

Two degenerated primers were designed based on the peptide sequence. Primer 1 contains the following sequence: TATTACTTTCCNAAYTAYCA where N represents a mixture of all four nucleotides (A, T, C and G) and Y represents a mixture of T and C only. Primer 2 contains the following sequence: TCGTATGGCATNACCTGNCC.

For isolation of genomic DNA encoding phenol oxidizing enzyme, DNA isolated from *Stachybotrys chartarum* (MUCL #38898) was used as a template for PCR. The DNA was diluted 100 fold with Tris-EDTA buffer to a final concentration of 88 ng/ul. Ten microliter of diluted DNA was added to the reaction mixture which contained 0.2 mM of each nucleotide (A, G, C and T), 1× reaction buffer, 0.296 microgram of primer 1 and 0.311 microgram of primer 2 in a total of 100 microliter reaction. After heating the mixture at 100° C. for 5 minutes, 2.5 units of Taq DNA polymerase was added to the reaction mix. The PCR reaction was performed at 95° C. for 1 minute, the primers were annealed to the template at 45° C. for 1 minute and extension was done at 68° C. for 1 minute. This cycle was repeated 30 times to achieve a gel-visible PCR fragment. The PCR fragment detected by agarose gel contained a fragment of about 1 kilobase which was then cloned into the plasmid vector pCR-II (Invitrogen). The 1 kb insert was then subjected to nucleic acid sequencing. The sequence data revealed that it was the gene encoding *Stachybotrys chartarum* because the deduced peptide sequence matched the peptide sequences disclosed above sequenced via Edman degradation. The PCR fragments containing the 5' gene and 3' gene were then isolated and sequenced. FIG. 2 provides the full length genomic sequence (SEQ ID NO:3) of *Stachybotrys* oxidase including the promoter and terminator sequences.

EXAMPLE 8

Cloning the cDNA Encoding *Stachybotrys* Phenol Oxidizing Enzyme

*Stachybotrys chartarum* strain (MUCL 38898) was grown in laccase production medium and RNA was extracted from mycellium and used as a template for cDNA isolation. The total cDNA was synthesized by reverse transcriptase using 4.3 microgram of RNA in a 20 microliter reaction containing 0.34 microgram oligo $dT_{18}$ primer, 0.5 mM of each of four nucleotides (A, G, C and T), 20 units of RNA inhibitor and 100 units of reverse transcriptase. The cDNA encoding the *Stachybotrys* phenol oxidizing enzyme was then cloned by PCR in two steps. First, the 5' cDNA was cloned as a 678 bp fragment using the following two primers: GTCAATATGCTGTTCAAG and CTCGCCATAGCCACTAGG. Second, the 3' cDNA was cloned as a 1301 bp fragment using following two primers: CTTTCGATGGTTGGGCTG and GTTCTAGACTACTCCTCGATTCCAAGATC. The cDNA sequence of 1791 bp is shown in FIG. 1.

EXAMPLE 9

Comparison of the *Stachybotrys chartarum* Phenol Oxidizing Enzyme Genomic DNA and cDNA A comparison of the cDNA with genomic DNA revealed that there were five introns in the genomic DNA. The protein translation start site (ATG) is at nucleotide #1044 to #1046 and the translation stop site is at nucleotide #3093 to #3095. Protein sequence translated from cDNA and genomic DNA contains 594 amino acids.

Comparison of the *Stachybotrys chartarum* Phenol Oxidizing Enzyme with Other Oxidizing Enzymes The protein sequence SEQ ID NO:2 was used as query to search GCG (Genetics Computer Group University Research Park, Madison Wis.) DNA and protein databases. It showed that *Stachybotrys* oxidase shared 60% identity to bilirubin oxidase at the protein sequence level. FIG. 3 shows the sequence alignment of the two proteins.

EXAMPLE 10

Expression of *Stachybotrys* Phenol Oxidizing Enzyme in *Aspergillus niger* var. *awamori*

Figure 6:
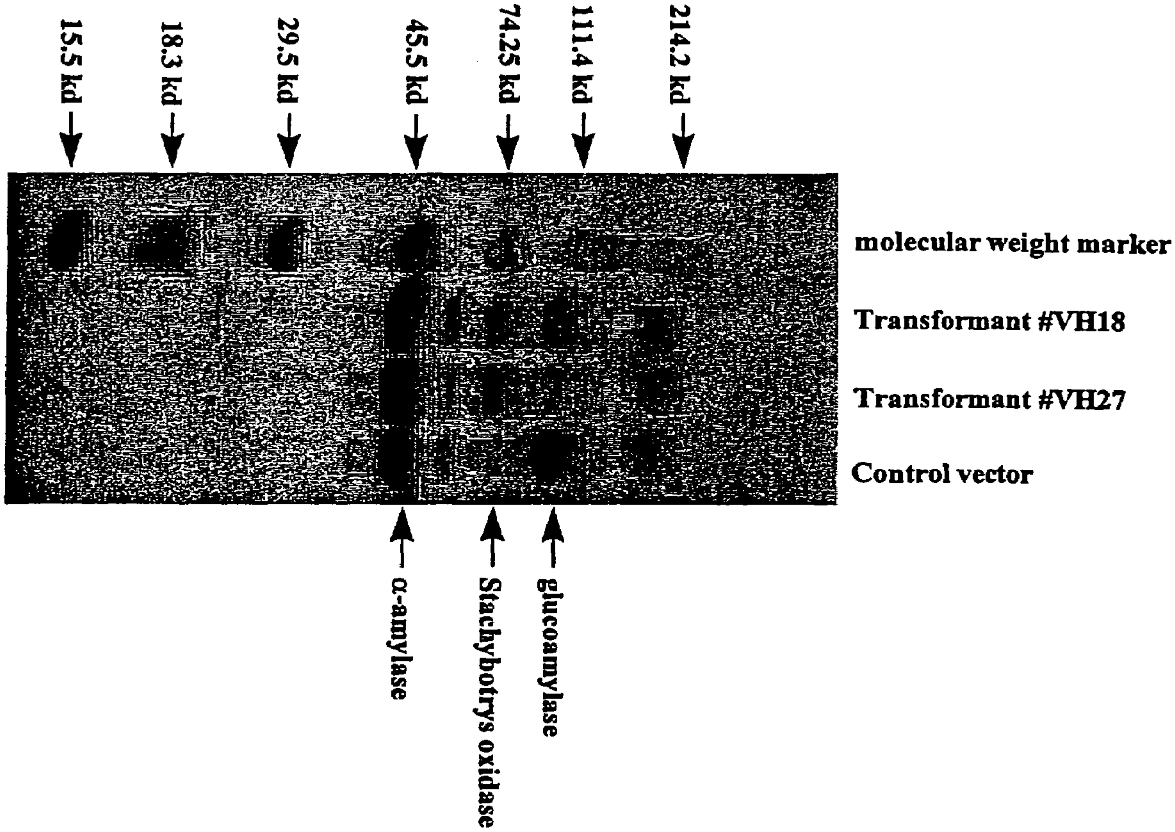
FIG. 6 is an SDS polyacrylamide gel electrophoresis showing the production of phenol oxidizing enzyme produced by *Aspergillus niger* var. *awamori.*

The DNA fragment containing nucleic acid encoding the *Stachybotrys* phenol oxidizing enzyme flanked by two newly introduced restriction enzyme sites (Bgl II and Xba I) was isolated by PCR (FIG. 5). This PCR fragment was first cloned into the plasmid vector pCR-II and subjected to nucleic acid sequencing to verify the gene sequence. This DNA fragment was then cloned into the Bgl II to Xba I site of vector (pGAPT, see FIG. 4). The vector used for expressing the *Stachybotrys* phenol oxidizing enzyme contains the *Aspergillus niger* glucoamylase gene promoter (from bases 1 to 1134) and terminator (from bases 1227 to 1485), a multicloning site (from bases 1135 to 1227), *Aspergillus nidulans* pyrG gene (from bases 1486 to 3078) as selection marker for fungal transformation and puc18 plasmid backbone for propagation in *E. coli*. The expression plasmid designated as pGAPT-gDO104 was then transformed into *Aspergillus* (strain dgr246:p2, Appl. Micro. Biotechnol, 1993, 39:738–743) by standard PEG methods. Transformants were selected on plates without uridine. Forty transformants were grown on CSA plates and then transferred to shake flasks containing CSL special medium with maltose. CSA plates contain: NaH2PHO4.H2O: 1 g/l; MgSO4: 1 g/l; Maltose: 50 g/l; Glucose: 2 g/l; Promosoy: 10 g/l; Mazu: 1 ml/l; and Bacto Agar: 15 g/l. CSL medium is described in Dunn-Coleman et al., 1991, Bio/Technology 9:976–981. CSL special medium is CSL medium with the glucose and fructose eliminated. ABTS assays were performed at days 3, 6, and 10. The transformants were also grown in CSL first and then transferred after 1 day's growth to Clofine-special medium. After 6 days growth, these samples were assayed for ABTS activities (>0.2 units). Five best transformants were spore purified and tested again for ABTS activity (>5 units/ml) after 8 day growth in Clofine medium. FIG. 6 shows a SDS-protein polyacrylamide gel indicated the expression level of the recombinant *Stachybotrys* oxidase in *Aspergillus niger* var. *awamori* grown of a 6 day culture grown in CSL special medium.

EXAMPLE 11

Expression of Phenol Oxidizing Enzyme in *Trichoderma reesei*

The expression plasmid for use in transforming *Trichoderma reesei* was constructed as follows. The ends of the BglII to XbaI fragment shown in FIG. 5 containing the gene encoding the *Stachybotrys* phenol oxidizing enzyme were blunted by T4 DNA polymerase and inserted into PmeI restriction site of the *Trichoderma* expression vector, pTrex, which is a modified version of pTEX, see PCT Publication No. WO 96/23928 for a complete description of the preparation of the pTEX vector, which discussion is herein incorporated by reference, which contains a CBHI promoter and terminater for gene expression and a *Trichoderma* pyr4 gene as a selection marker for transformants. The linear DNA fragment containing only the CBH1 promoter, the *Stachybotrys* phenol oxidizing gene, the CBH1 terminater and selection marker pyr4 was isolated from a gel and was used to transform a uridine auxotroph strain of *Trichoderma reesei* (see U.S. Pat. No. 5,472,864) which has the four major cellulase genes deleted. Stable transformants were isolated on *Trichoderma* minimal plates without uridine. The transformants were grown on 50 ml of Proflo medium in shake flasks for 4 days at 28° C. to 30° C. and expression of the phenol oxidizing enzyme was assayed by ABTS (>2 units/ml) and SDS-PAGE protein gel. Proflo medium is composed of (g/l) Proflo 22.5; lactose 30.0; $(NH_4)_2SO_4$ 6.5 $KH_2PO_4$ 2.0; $MgSO_4.7H_2O$ 0.3; $CaCL_2$ 0.2; $CaCO_3$ 0.72; trace metal stock solution 1.0 ml/l and 10% Tween 80 2.0 ml/l. The trace metal stock solution used had (g/l) $FeSO_4.7H_2O$ 5.0; $MnSO_4.H_2O$ 1.6; $ZnSO_4.7H_2O$ 1.4; $CoCl_2.6H_2O$) 2.8.

EXAMPLE 12

Expression of *Stachybotrys* Phenol Oxidizing Enzyme in *Saccharomyces cerevisiae*

The BglII to XbaI fragment of the cDNA (SEQ ID NO:1) of the phenol oxidizing gene was cloned into yeast expression vector yES2.0 (Invitrogen) which contains the yeast Gal 1 promoter and Cyc 1 terminator, to control expression of the phenol oxidizing gene, and the yeast URA3 gene as a selection marker. The expression plasmid was transformed into a yeast strain (Invitrogen Sc2 strain). The transformants were selected on yeast minimal plate without uridine. Four randomly picked transformants showed activity in plate assay (colored halo formation in yeast minimal plate with 1 mM ABTS) while the control plasmid vector did not show any colored halo formation.

I claim:

1. An isolated color-modifying oxidase obtainable from *Stachybotrys* and having at least 95% identity to the color-modifying oxidase enzyme having the amino acid sequence disclosed in SEQ ID NO:2, wherein said oxidase is capable of oxidizing 2,2'-azino-bis-(3-ethylbenzothiazoline-6-sulfonate).

2. The color-modifying oxidase of claim 1 wherein said *Stachybotrys* is *S. chartarum.*

3. The color-modifying oxidase of claim 1 having the amino acid sequence disclosed in SEQ ID NO:2.

4. The color-modifying oxidase of claim 1, wherein said oxidase consists of the amino acid sequence disclosed in SEQ ID NO:2.

* * * * *

SEQUENCE LISTING

<160> NUMBER OF SEQ ID NOS: 5

<210> SEQ ID NO 1
<211> LENGTH: 1791
<212> TYPE: DNA
<213> ORGANISM: Stachybotrys sp.

<400> SEQUENCE: 1

```
gtcaatatgc tgttcaagtc atggcaactg gcagcagcct ccgggctcct gtctggagtc     60

ctcggcatcc cgatggacac cggcagccac cccattgagg ctgttgatcc cgaagtgaag    120

actgaggtct tcgctgactc cctccttgct gcagcaggcg atgacgactg ggagtcacct    180

ccatacaact tgctttacag gaatgccctg ccaattccac ctgtcaagca gcccaagatg    240

atcattacca accctgtcac cggcaaggac atttggtact atgagatcga gatcaagcca    300

tttcagcaaa ggatttaccc caccttgcgc cctgccactc tcgtcggcta cgatggcatg    360

agccctggtc ctactttcaa tgttcccaga ggaacagaga ctgtagttag gttcatcaac    420

aatgccaccg tggagaactc ggtccatctg cacggctccc catcgcgtgc ccctttcgat    480

ggttgggctg aagatgtgac cttccctggc gagtacaagg attactactt tcccaactac    540

caatccgccc gccttctgtg gtaccatgac cacgctttca tgaagactgc tgagaatgcc    600

tactttggtc aggctggcgc ctacattatc aacgacgagg ctgaggatgc tctcggtctt    660

cctagtggct atggcgagtt cgatatccct ctgatcctga cggccaagta ctataacgcc    720

gatggtaccc tgcgttcgac cgagggtgag gaccaggacc tgtggggaga tgtcatccat    780

gtcaacggac agccatggcc tttccttaac gtccagcccc gcaagtaccg tttccgattc    840

ctcaacgctg ccgtgtctcg tgcttggctc ctctacctcg tcaggaccag ctctcccaac    900

gtcagaattc ctttccaagt cattgcctct gatgctggtc tccttcaagc ccccgttcag    960

acctctaacc tctaccttgc tgttgccgag cgttacgaga tcattattga cttcaccaac   1020

tttgctggcc agactcttga cctgcgcaac gttgctgaga ccaacgatgt cggcgacgag   1080

gatgagtacg ctcgcactct cgaggtgatg cgcttcgtcg tcagctctgg cactgttgag   1140

gacaacagcc aggtcccctc cactctccgt gacgttcctt tccctcctca caaggaaggc   1200

cccgccgaca agcacttcaa gtttgaacgc agcaacggac actacctgat caacgatgtt   1260

ggctttgccg atgtcaatga gcgtgtcctg gccaagcccg agctcggcac cgttgaggtc   1320

tgggagctcg agaactcctc tggaggctgg agccaccccg tccacattca ccttgttgac   1380

ttcaagatcc tcaagcgaac tggtggtcgt ggccaggtca tgccctacga gtctgctggt   1440

cttaaggatg tcgtctggtt gggcaggggt gagaccctga ccatcgaggc ccactaccaa   1500

ccctggactg gagcttacat gtggcactgt cacaacctca ttcacgagga taacgacatg   1560

atggctgtat tcaacgtcac cgccatggag gagaagggat atcttcagga ggacttcgag   1620

gaccccatga accccaagtg gcgcgccgtt ccttacaacc gcaacgactt ccatgctcgc   1680

gctggaaact tctccgccga gtccatcact gcccgagtgc aggagctggc cgagcaggag   1740

ccgtacaacc gcctcgatga gatcctggag gatcttggaa tcgaggagta a             1791
```

<210> SEQ ID NO 2
<211> LENGTH: 594
<212> TYPE: PRT
<213> ORGANISM: Stachybotrys sp.

<400> SEQUENCE: 2

-continued

```
Met Leu Phe Lys Ser Trp Gln Leu Ala Ala Ala Ser Gly Leu Leu Ser
 1               5                  10                  15

Gly Val Leu Gly Ile Pro Met Asp Thr Gly Ser His Pro Ile Glu Ala
            20                  25                  30

Val Asp Pro Glu Val Lys Thr Glu Val Phe Ala Asp Ser Leu Leu Ala
        35                  40                  45

Ala Ala Gly Asp Asp Asp Trp Glu Ser Pro Pro Tyr Asn Leu Leu Tyr
    50                  55                  60

Arg Asn Ala Leu Pro Ile Pro Pro Val Lys Gln Pro Lys Met Ile Ile
65                  70                  75                  80

Thr Asn Pro Val Thr Gly Lys Asp Ile Trp Tyr Tyr Glu Ile Glu Ile
                85                  90                  95

Lys Pro Phe Gln Gln Arg Ile Tyr Pro Thr Leu Arg Pro Ala Thr Leu
            100                 105                 110

Val Gly Tyr Asp Gly Met Ser Pro Gly Pro Thr Phe Asn Val Pro Arg
        115                 120                 125

Gly Thr Glu Thr Val Val Arg Phe Ile Asn Asn Ala Thr Val Glu Asn
    130                 135                 140

Ser Val His Leu His Gly Ser Pro Ser Arg Ala Pro Phe Asp Gly Trp
145                 150                 155                 160

Ala Glu Asp Val Thr Phe Pro Gly Glu Tyr Lys Asp Tyr Tyr Phe Pro
                165                 170                 175

Asn Tyr Gln Ser Ala Arg Leu Leu Trp Tyr His Asp His Ala Phe Met
            180                 185                 190

Lys Thr Ala Glu Asn Ala Tyr Phe Gly Gln Ala Gly Ala Tyr Ile Ile
        195                 200                 205

Asn Asp Glu Ala Glu Asp Ala Leu Gly Leu Pro Ser Gly Tyr Gly Glu
    210                 215                 220

Phe Asp Ile Pro Leu Ile Leu Thr Ala Lys Tyr Tyr Asn Ala Asp Gly
225                 230                 235                 240

Thr Leu Arg Ser Thr Glu Gly Glu Asp Gln Asp Leu Trp Gly Asp Val
                245                 250                 255

Ile His Val Asn Gly Gln Pro Trp Pro Phe Leu Asn Val Gln Pro Arg
            260                 265                 270

Lys Tyr Arg Phe Arg Phe Leu Asn Ala Ala Val Ser Arg Ala Trp Leu
        275                 280                 285

Leu Tyr Leu Val Arg Thr Ser Ser Pro Asn Val Arg Ile Pro Phe Gln
    290                 295                 300

Val Ile Ala Ser Asp Ala Gly Leu Leu Gln Ala Pro Val Gln Thr Ser
305                 310                 315                 320

Asn Leu Tyr Leu Ala Val Ala Glu Arg Tyr Glu Ile Ile Ile Asp Phe
                325                 330                 335

Thr Asn Phe Ala Gly Gln Thr Leu Asp Leu Arg Asn Val Ala Glu Thr
            340                 345                 350

Asn Asp Val Gly Asp Glu Asp Glu Tyr Ala Arg Thr Leu Glu Val Met
        355                 360                 365

Arg Phe Val Val Ser Ser Gly Thr Val Glu Asp Asn Ser Gln Val Pro
    370                 375                 380

Ser Thr Leu Arg Asp Val Pro Phe Pro Pro His Lys Glu Gly Pro Ala
385                 390                 395                 400

Asp Lys His Phe Lys Phe Glu Arg Ser Asn Gly His Tyr Leu Ile Asn
                405                 410                 415
```

-continued

```
Asp Val Gly Phe Ala Asp Val Asn Glu Arg Val Leu Ala Lys Pro Glu
            420                 425                 430

Leu Gly Thr Val Glu Val Trp Glu Leu Glu Asn Ser Ser Gly Gly Trp
        435                 440                 445

Ser His Pro Val His Ile His Leu Val Asp Phe Lys Ile Leu Lys Arg
    450                 455                 460

Thr Gly Gly Arg Gly Gln Val Met Pro Tyr Glu Ser Ala Gly Leu Lys
465                 470                 475                 480

Asp Val Val Trp Leu Gly Arg Gly Glu Thr Leu Thr Ile Glu Ala His
                485                 490                 495

Tyr Gln Pro Trp Thr Gly Ala Tyr Met Trp His Cys His Asn Leu Ile
            500                 505                 510

His Glu Asp Asn Asp Met Met Ala Val Phe Asn Val Thr Ala Met Glu
        515                 520                 525

Glu Lys Gly Tyr Leu Gln Glu Asp Phe Glu Asp Pro Met Asn Pro Lys
    530                 535                 540

Trp Arg Ala Val Pro Tyr Asn Arg Asn Asp Phe His Ala Arg Ala Gly
545                 550                 555                 560

Asn Phe Ser Ala Glu Ser Ile Thr Ala Arg Val Gln Glu Leu Ala Glu
                565                 570                 575

Gln Glu Pro Tyr Asn Arg Leu Asp Glu Ile Leu Glu Asp Leu Gly Ile
            580                 585                 590

Glu Glu
```

<210> SEQ ID NO 3
<211> LENGTH: 3677
<212> TYPE: DNA
<213> ORGANISM: Stachybotrys chartarum

<400> SEQUENCE: 3

```
ctggctagcc tcacttggta gacagccctg acagcctcac tggctggggg tcgaaaggcc     60

agtcaatatc ttggtcactg ctaatagttc cttgctacgc gcaaaaagct ccttgccgaa    120

ggggcacaga ctatcaagtg agacatatag gatgcatgtc tttcatagcc acagttaggg    180

tggtgaccta ctcgaagagg ccccgacttg catgcatacg acatgtcgct tccatgcaac    240

atgtatgcgc acatcggcga tcaggcaccc tctgcatgca gaatagaacc cccctggttt    300

ccttttgttt cttttccttt ctcaacgacg cgtgagcgtg gttaacttga gcaaggccga    360

gtggtctgtt cacgaggtta ccatcgaact ctcttctttc ccaatcatga cctgcccccc    420

gagtttagcc cccatcacgg ctgtgaaatc cacttcgata atcctagcct agtgctactc    480

ttcaatagtt gctcctgatg gggcactttg gtcacattgc cttggttyct cctacctcgt    540

tctcttccgc atcaagcctc tatgcccgac gacaacacct cattggcccg gaccactttg    600

agcgcgcacg caccttcgcg ccgaaggagt tgataacacc cttcaccctt gcccaatgat    660

ggagttttgg tctatttgtc atgatcacct cacattcact agatcacgga tcctggaaga    720

gggtgtggaa gccagaccag cttgtccctg ttcttgcaga ctcaggtcag ctcctagcgg    780

ctatcacagc tcaggattat caagtcccgt aaagtccaga cccttttcat tgtatgatgc    840

tgcctaattt gcgctatctc tatgccgtag cagccgtctt ggctacaact ggctgccatg    900

gctgaagcat cgtgagatct ataaaggtct ccgaatcctc ggtgaagtca gaatcgtctc    960

tccacaccag tcaacaacaa gcttctttct cttacagctt agcctgagca cattcacaga   1020

actcttccct tcttttcgtc aatatgctgt tcaagtcatg gcaactggca gcagcctccg   1080
```

-continued

```
ggctcctgtc tggagtcctc ggcatcccga tggacaccgg cagccacccc attgaggctg   1140
ttgatcccga agtgaagact gaggtcttcg ctgactccct ccttgctgca gcaggcgatg   1200
acgactggga gtcacctcca tacaacttgc tttacaggtg agacacctgt cccacctgtt   1260
ttccctcgat aactaactct tataggaatg ccctgccaat tccacctgtc aagcagccca   1320
agatgtatgt ctttgatttt ctacgaagca actcggcccc gactaatgta ttctaggatc   1380
attaccaacc ctgtcaccgg caaggacatt tggtactatg agatcgagat caagccattt   1440
cagcaaaggg tgagtttgct cagaaacctt gtggtaatta atcattgtta ctgacccttt   1500
cagatttacc ccaccttgcg ccctgccact ctcgtcggct acgatggcat gagccctggt   1560
cctactttca atgttcccag aggaacagag actgtagtta ggttcatcaa caatgccacc   1620
gtggagaact cggtccatct gcacggctcc ccatcgcgtg ccccttttcga tggttgggct   1680
gaagatgtga ccttccctgg cgagtacaag gattactact ttcccaacta ccaatccgcc   1740
cgccttctgt ggtaccatga ccacgctttc atgaaggtat gctacgagcc tttatctttc   1800
ttggctacct ttggctaacc aacttccttt cgtagactgc tgagaatgcc tactttggtc   1860
aggctggcgc ctacattatc aacgacgagg ctgaggatgc tctcggtctt cctagtggct   1920
atggcgagtt cgatatccct ctgatcctga cggccaagta ctataacgcc gatggtaccc   1980
tgcgttcgac cgagggtgag gaccaggacc tgtggggaga tgtcatccat gtcaacggac   2040
agccatggcc tttccttaac gtccagcccc gcaagtaccg tttccgattc ctcaacgctg   2100
ccgtgtctcg tgcttggctc ctctacctcg tcaggaccag ctctcccaac gtcagaattc   2160
ctttccaagt cattgcctct gatgctggtc tccttcaagc cccgttcag acctctaacc   2220
tctaccttgc tgttgccgag cgttacgaga tcattattgg tatgccctcc cctctcacga   2280
atgagtcaag aactctaaga ctaacacttg tagacttcac caactttgct ggccagactc   2340
ttgacctgcg caacgttgct gagaccaacg atgtcggcga cgaggatgag tacgctcgca   2400
ctctcgaggt gatgcgcttc gtcgtcagct ctggcactgt tgaggacaac agccaggtcc   2460
cctccactct ccgtgacgtt cctttccctc ctcacaagga aggccccgcc gacaagcact   2520
tcaagtttga acgcagcaac ggacactacc tgatcaacga tgttggcttt gccgatgtca   2580
atgagcgtgt cctggccaag cccgagctcg gcaccgttga ggtctgggag ctcgagaact   2640
cctctggagg ctggagccac cccgtccaca ttcaccttgt tgacttcaag atcctcaagc   2700
gaactggtgg tcgtggccag gtcatgccct acgagtctgc tggtcttaag gatgtcgtct   2760
ggttgggcag ggtgagacc ctgaccatcg aggcccacta ccaaccctgg actggagctt   2820
acatgtggca ctgtcacaac ctcattcacg aggataacga catgatggct gtattcaacg   2880
tcaccgccat ggaggagaag ggatatcttc aggaggactt cgaggacccc atgaacccca   2940
agtggcgcgc cgttccttac aaccgcaacg acttccatgc tcgcgctgga aacttctccg   3000
ccgagtccat cactgcccga gtgcaggagc tggccgagca ggagccgtac aaccgcctcg   3060
atgagatcct ggaggatctt ggaatcgagg agtaaacccc gagccacaag ctctacaatc   3120
gttttgagtc ttaagacgag gctcttggtg cgtattcttt tcttccctac ggggaactcc   3180
gctgtccact gcgatgtgaa ggaccatcac aaagcaacgt atatattgga ctcaccactg   3240
tcattaccgc ccacttgtac ctattcgatt cttgttcaaa cttttctagt gcgagagtgt   3300
ccatagtcaa gaaacgccca tagggctatc gtctaaactg aactattgtg tggtctgtga   3360
cgtggagtag atgtcaattg tgatgagaca cagtaaatac ggtatatctt ttcctaggac   3420
tacaggatca gtttctcatg agattacatc cgtctaatgt ttgtccatga gagtctagct   3480
```

-continued

```
aaggttgaga atgcatcaga cggaatcatt tgatgctctc agctcgtatt accgatgtaa   3540

gacaagttag gtaagttgct tggtatccga aaatgactca ggctccctca ttaggttgca   3600

tgtgaaaacc ttcagcaact catgggtgtt gggaccaaat catccatacc tgattttgat   3660

aactgacctg ggtcaat                                                  3677


<210> SEQ ID NO 4
<211> LENGTH: 568
<212> TYPE: PRT
<213> ORGANISM: Bilirubin oxidase

<400> SEQUENCE: 4

Met Phe Lys His Thr Leu Gly Ala Ala Ala Leu Ser Leu Leu Phe Asn
 1               5                  10                  15

Ser Asn Ala Val Gln Ala Ser Pro Val Pro Glu Thr Ser Pro Ala Thr
            20                  25                  30

Gly His Leu Phe Lys Arg Val Ala Gln Ile Ser Pro Gln Tyr Pro Met
        35                  40                  45

Phe Thr Val Pro Leu Pro Ile Pro Pro Val Lys Gln Pro Arg Leu Thr
    50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
    130                 135                 140

Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
                165                 170                 175

His Ile Thr Ala Glu Asn Ala Tyr Arg Gly Gln Ala Gly Leu Tyr Met
            180                 185                 190

Leu Thr Asp Pro Ala Glu Asp Ala Leu Asn Leu Pro Ser Gly Tyr Gly
        195                 200                 205

Glu Phe Asp Ile Pro Met Ile Leu Thr Ser Lys Gln Tyr Thr Ala Asn
    210                 215                 220

Gly Asn Leu Val Thr Thr Asn Gly Glu Leu Asn Ser Phe Trp Gly Asp
225                 230                 235                 240

Val Ile His Val Asn Gly Gln Pro Trp Pro Phe Lys Asn Val Glu Pro
                245                 250                 255

Arg Lys Tyr Arg Phe Arg Phe Leu Asp Ala Ala Val Ser Arg Ser Phe
            260                 265                 270

Gly Leu Tyr Phe Ala Asp Thr Asp Ala Ile Asp Thr Arg Leu Pro Phe
        275                 280                 285

Lys Val Ile Ala Ser Asp Ser Gly Leu Leu Glu His Pro Ala Asp Thr
    290                 295                 300

Ser Leu Leu Tyr Ile Ser Met Ala Glu Arg Tyr Glu Val Val Phe Asp
305                 310                 315                 320

Phe Ser Asp Tyr Ala Gly Lys Thr Ile Glu Leu Arg Asn Leu Gly Gly
                325                 330                 335
```

-continued

```
Ser Ile Gly Gly Ile Gly Thr Asp Thr Asp Tyr Asp Asn Thr Asp Lys
            340                 345                 350

Val Met Arg Phe Val Val Ala Asp Asp Thr Thr Gln Pro Asp Thr Ser
        355                 360                 365

Val Val Pro Ala Asn Leu Arg Asp Val Pro Phe Pro Ser Pro Thr Thr
    370                 375                 380

Asn Arg Gln Phe Arg Phe Gly Arg Thr Gly Pro Thr Trp Thr Ile Asn
385                 390                 395                 400

Gly Val Ala Phe Ala Asp Val Gln Asn Arg Leu Leu Ala Asn Val Pro
                405                 410                 415

Val Gly Thr Val Glu Arg Trp Glu Leu Ile Asn Ala Gly Asn Gly Trp
            420                 425                 430

Thr His Pro Ile His Ile His Leu Val Asp Phe Lys Val Ile Ser Arg
        435                 440                 445

Thr Ser Gly Asn Asn Ala Arg Thr Val Met Pro Tyr Glu Ser Lys Asp
    450                 455                 460

Val Val Trp Leu Gly Arg Arg Glu Thr Val Val Val Glu Ala His Tyr
465                 470                 475                 480

Ala Pro Phe Pro Gly Val Tyr Met Phe His Cys His Asn Leu Ile His
                485                 490                 495

Glu Asp His Asp Met Met Ala Ala Phe Asn Ala Thr Val Leu Pro Asp
            500                 505                 510

Tyr Gly Tyr Asn Ala Thr Val Phe Val Asp Pro Met Glu Glu Leu Trp
        515                 520                 525

Gln Ala Arg Pro Tyr Glu Leu Gly Glu Phe Gln Ala Gln Ser Gly Gln
    530                 535                 540

Phe Ser Val Gln Ala Val Thr Glu Arg Ile Gln Thr Met Ala Glu Tyr
545                 550                 555                 560

Arg Pro Tyr Ala Ala Ala Asp Glu
                565


<210> SEQ ID NO 5
<211> LENGTH: 2067
<212> TYPE: DNA
<213> ORGANISM: Artificial Sequence
<220> FEATURE:
<223> OTHER INFORMATION: plasmid

<400> SEQUENCE: 5

agatctaata tgctgttcaa gtcatggcaa ctggcagcag cctccgggct cctgtctgga     60

gtcctcggca tcccgatgga caccggcagc caccccattg aggctgttga tcccgaagtg    120

aagactgagg tcttcgctga ctccctcctt gctgcagcag gcgatgacga ctgggagtca    180

cctccataca acttgcttta caggtgagac acctgtccca cctgttttcc ctcgataact    240

aactcttata ggaatgccct gccaattcca cctgtcaagc agcccaagat gtatgtcttt    300

gattttctac gaagcaactc ggccccgact aatgtattct aggatcatta ccaaccctgt    360

caccggcaag gacatttggt actatgagat cgagatcaag ccatttcagc aaagggtgag    420

tttgctcaga aaccttgtgg taattaatca ttgttactga ccctttcaga tttaccccac    480

cttgcgccct gccactctcg tcggctacga tggcatgagc cctggtccta ctttcaatgt    540

tcccagagga acagagactg tagttaggtt catcaacaat gccaccgtgg agaactcggt    600

ccatctgcac ggctccccat cgcgtgcccc tttcgatggt tgggctgaag atgtgacctt    660

ccctggcgag tacaaggatt actactttcc caactaccaa tccgcccgcc ttctgtggta    720
```

-continued

```
ccatgaccac gctttcatga aggtatgcta cgagccttta tctttcttgg ctacctttgg    780
ctaaccaact tcctttcgta gactgctgag aatgcctact ttggtcaggc tggcgcctac    840
attatcaacg acgaggctga ggatgctctc ggtcttccta gtggctatgg cgagttcgat    900
atccctctga tcctgacggc caagtactat aacgccgatg gtaccctgcg ttcgaccgag    960
ggtgaggacc aggacctgtg gggagatgtc atccatgtca acggacagcc atggcctttc   1020
cttaacgtcc agccccgcaa gtaccgtttc cgattcctca acgctgccgt gtctcgtgct   1080
tggctcctct acctcgtcag gaccagctct cccaacgtca gaattccttt ccaagtcatt   1140
gcctctgatg ctggtctcct tcaagccccc gttcagacct ctaacctcta ccttgctgtt   1200
gccgagcgtt acgagatcat tattggtatg ccctcccctc tcacgaatga gtcaagaact   1260
ctaagactaa cacttgtaga cttcaccaac tttgctggcc agactcttga cctgcgcaac   1320
gttgctgaga ccaacgatgt cggcgacgag gatgagtacg ctcgcactct cgaggtgatg   1380
cgcttcgtcg tcagctctgg cactgttgag gacaacagcc aggtcccctc cactctccgt   1440
gacgttcctt tccctcctca caaggaaggc cccgccgaca agcacttcaa gtttgaacgc   1500
agcaacggac actacctgat caacgatgtt ggctttgccg atgtcaatga gcgtgtcctg   1560
gccaagcccg agctcggcac cgttgaggtc tgggagctcg agaactcctc tggaggctgg   1620
agccaccccg tccacattca ccttgttgac ttcaagatcc tcaagcgaac tggtggtcgt   1680
ggccaggtca tgccctacga gtctgctggt cttaaggatg tcgtctggtt gggcaggggt   1740
gagaccctga ccatcgaggc ccactaccaa ccctggactg gagcttacat gtggcactgt   1800
cacaacctca ttcacgagga taacgacatg atggctgtat tcaacgtcac cgccatggag   1860
gagaagggat atcttcagga ggacttcgag gaccccatga accccaagtg gcgcgccgtt   1920
ccttacaacc gcaacgactt ccatgctcgc gctggaaact tctccgccga gtccatcact   1980
gcccgagtgc aggagctggc cgagcaggag ccgtacaacc gcctcgatga gatcctggag   2040
gatcttggaa tcgaggagta gtctaga                                       2067
```